(12) United States Patent
Rabiner et al.

(10) Patent No.: US 7,503,895 B2
(45) Date of Patent: *Mar. 17, 2009

(54) ULTRASONIC DEVICE FOR TISSUE ABLATION AND SHEATH FOR USE THEREWITH

(75) Inventors: Robert A. Rabiner, Chelmsford, MA (US); Bradley A. Hare, Chelmsford, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 872 days.

This patent is subject to a terminal disclaimer.

(21) Appl. No.: 10/373,134

(22) Filed: Feb. 24, 2003

(65) Prior Publication Data

US 2003/0176791 A1    Sep. 18, 2003

Related U.S. Application Data

(63) Continuation of application No. 09/784,619, filed on Feb. 15, 2001, now Pat. No. 6,524,251, which is a continuation-in-part of application No. 09/618,352, filed on Jul. 19, 2000, now Pat. No. 6,551,337.

(60) Provisional application No. 60/178,901, filed on Jan. 28, 2000, provisional application No. 60/157,824, filed on Oct. 5, 1999.

(51) Int. Cl.
*A61B 8/00* (2006.01)
*A61B 8/14* (2006.01)

(52) U.S. Cl. .................................... 600/439; 600/459
(58) Field of Classification Search ............... 600/439, 600/459, 437; 606/169, 171
See application file for complete search history.

(56) References Cited

U.S. PATENT DOCUMENTS

| 168,975 A | 10/1875 | Farmer |
| 323,762 A | 8/1885 | White |
| 404,319 A | 5/1889 | Taylor |
| 414,090 A | 10/1889 | Taylor |
| 1,045,326 A | 11/1912 | Ruflin |
| 1,239,451 A | 9/1917 | Belz |
| 1,779,478 A | 10/1930 | Leech |

(Continued)

FOREIGN PATENT DOCUMENTS

CA    2251096    8/1998

(Continued)

OTHER PUBLICATIONS

PCT International Search Report for International Application No. PCT/US02/22517 dated Oct. 18, 2002.

(Continued)

*Primary Examiner*—Eric F Winakur
*Assistant Examiner*—Jacqueline Cheng
(74) *Attorney, Agent, or Firm*—Fish & Richardson P.C.

(57) ABSTRACT

A transverse mode ultrasonic probe is provided which creates a cavitation area along its longitudinal length, increasing the working surface of the probe. Accessory sheaths are also provided for use with the probe to enable a user to select from features most suited to an individual medical procedure. The sheaths provide acoustic enhancing and aspiration enhancing properties, and/or can be used as surgical tools or as medical access devices, protecting tissue from physical contact with the probe.

25 Claims, 7 Drawing Sheets

U.S. PATENT DOCUMENTS

| | | | |
|---|---|---|---|
| 1,861,769 A | 6/1932 | Wappler | |
| 2,199,602 A | 5/1940 | Wright | |
| 2,242,120 A | 5/1941 | Gardiner | |
| 2,270,922 A | 1/1942 | Bechmann et al. | |
| 2,321,358 A | 6/1943 | Bokovoy | |
| 2,514,080 A | 7/1950 | Mason | |
| 2,742,076 A | 4/1956 | Klein | |
| 2,838,695 A | 6/1958 | Thurston | |
| 2,843,176 A | 6/1958 | Franck | |
| 2,917,691 A | 12/1959 | De Prisco et al. | |
| 2,990,616 A | 7/1961 | Balamuth et al. | 433/119 |
| 3,056,698 A | 10/1962 | Kleesattel et al. | |
| 3,089,790 A | 5/1963 | Balamuth et al. | |
| 3,113,225 A | 12/1963 | Kleesattel et al. | |
| 3,132,548 A | 5/1964 | Livermont | |
| 3,133,351 A | 5/1964 | von Seggern | |
| 3,202,021 A | 8/1965 | Livermont | |
| 3,241,780 A | 3/1966 | Kitselman | |
| 3,304,449 A | 2/1967 | Pohlman et al. | |
| 3,315,663 A | 4/1967 | Goldfarb | |
| 3,401,446 A | 9/1968 | Obeda et al. | |
| 3,433,226 A | 3/1969 | Boyd | |
| 3,438,824 A | 4/1969 | Balamuth | |
| 3,486,361 A | 12/1969 | Vaneman et al. | |
| 3,524,085 A | 8/1970 | Shoh | |
| 3,526,219 A | 9/1970 | Balamuth | 600/565 |
| 3,528,410 A | 9/1970 | Banko | |
| 3,565,062 A | 2/1971 | Kuris | 606/169 |
| 3,589,363 A | 6/1971 | Banko | 604/22 |
| 3,614,484 A | 10/1971 | Shoh | |
| 3,660,186 A | 5/1972 | Sager et al. | |
| 3,683,736 A | 8/1972 | Loose | |
| 3,763,680 A | 10/1973 | Godfrey et al. | |
| 3,805,787 A | 4/1974 | Banko | 604/22 |
| 3,809,977 A | 5/1974 | Balamuth et al. | |
| 3,840,932 A | 10/1974 | Balamuth et al. | |
| 3,853,130 A | 12/1974 | Sheridan | |
| 3,861,391 A | 1/1975 | Antonevich et al. | 606/128 |
| 3,890,977 A | 6/1975 | Wilson | |
| 3,906,954 A | 9/1975 | Baehr et al. | |
| 3,939,033 A | 2/1976 | Grgach et al. | |
| 3,955,662 A | 5/1976 | Thackston | |
| 3,962,898 A | 6/1976 | Tillmann | |
| 3,967,621 A | 7/1976 | Schwarz | |
| 3,980,906 A | 9/1976 | Kuris et al. | |
| 3,988,782 A | 11/1976 | Dardik et al. | |
| 3,990,452 A | 11/1976 | Murry et al. | |
| 3,991,929 A | 11/1976 | Smith | |
| 4,011,474 A | 3/1977 | O'Neill | |
| 4,012,174 A | 3/1977 | Seibel et al. | |
| 4,012,647 A | 3/1977 | Balamuth et al. | |
| 4,044,174 A | 8/1977 | Carr | |
| 4,063,557 A | 12/1977 | Wuchinich et al. | |
| 4,069,541 A | 1/1978 | Williams et al. | |
| 4,083,996 A | 4/1978 | Tanaka et al. | |
| 4,136,700 A | 1/1979 | Broadwin et al. | 606/169 |
| 4,143,130 A | 3/1979 | Imondi et al. | |
| 4,144,646 A | 3/1979 | Takemoto et al. | |
| 4,157,396 A | 6/1979 | Tanaka et al. | |
| 4,164,524 A | 8/1979 | Ward et al. | |
| 4,169,984 A | 10/1979 | Parisi | |
| 4,174,410 A | 11/1979 | Smith | |
| 4,178,935 A | 12/1979 | Gekhman et al. | |
| 4,203,429 A | 5/1980 | Vasilevsky et al. | |
| 4,203,444 A | 5/1980 | Bonnell et al. | |
| 4,223,676 A | 9/1980 | Wuchinich et al. | |
| 4,225,803 A | 9/1980 | Goof | |
| 4,236,510 A | 12/1980 | Hatter et al. | 601/2 |
| 4,248,232 A | 2/1981 | Engelbrecht et al. | |
| 4,265,928 A | 5/1981 | Braun | |
| 4,280,233 A | 7/1981 | Raab | |
| 4,300,564 A | 11/1981 | Furihata | |
| 4,311,147 A | 1/1982 | Hausler | |
| 4,315,181 A | 2/1982 | Holze, Jr. | |
| 4,316,465 A | 2/1982 | Dotson, Jr. | |
| 4,326,903 A | 4/1982 | Summo | |
| 4,334,168 A | 6/1982 | Besson et al. | |
| 4,335,426 A | 6/1982 | Maxwell et al. | |
| 4,352,570 A | 10/1982 | Firth | |
| 4,356,590 A | 11/1982 | Goldsmith | |
| 4,363,992 A | 12/1982 | Holze, Jr. | |
| 4,368,410 A | 1/1983 | Hance et al. | |
| 4,385,413 A | 5/1983 | Goldsmith | |
| 4,393,734 A | 7/1983 | Thorn et al. | |
| 4,395,392 A | 7/1983 | Wolgemuth | |
| 4,399,003 A | 8/1983 | Sarig et al. | |
| 4,414,045 A | 11/1983 | Wang et al. | |
| 4,425,115 A | 1/1984 | Wuchinich | |
| 4,428,748 A | 1/1984 | Peyman et al. | |
| 4,445,509 A | 5/1984 | Auth | |
| 4,447,455 A | 5/1984 | Madaus et al. | |
| 4,462,242 A | 7/1984 | Morgenthaler | |
| 4,467,678 A | 8/1984 | Lindholm | |
| 4,474,180 A | 10/1984 | Angulo | 128/328 |
| 4,479,585 A | 10/1984 | Sandhaus | |
| 4,480,642 A | 11/1984 | Stoy et al. | |
| 4,483,571 A | 11/1984 | Mishiro | |
| 4,486,680 A | 12/1984 | Bonnet et al. | 310/323.19 |
| 4,493,694 A | 1/1985 | Wuchinich | 604/22 |
| 4,498,025 A | 2/1985 | Takahashi | |
| 4,504,264 A | 3/1985 | Kelman | 604/22 |
| 4,516,398 A | 5/1985 | Wuchinich | |
| 4,523,122 A | 6/1985 | Tone et al. | |
| 4,526,571 A | 7/1985 | Wuchinich | 604/22 |
| 4,529,115 A | 7/1985 | Renshaw et al. | |
| 4,530,138 A | 7/1985 | Ritter | |
| 4,534,819 A | 8/1985 | Payet et al. | |
| 4,535,659 A | 8/1985 | Yang | |
| 4,535,759 A | 8/1985 | Polk et al. | 128/24 A |
| 4,571,520 A | 2/1986 | Saito et al. | |
| 4,572,041 A | 2/1986 | Rissmann | |
| 4,576,177 A | 3/1986 | Webster, Jr. | |
| 4,583,365 A | 4/1986 | John | |
| 4,587,958 A | 5/1986 | Noguchi et al. | |
| 4,589,415 A | 5/1986 | Haaga | |
| 4,601,705 A | 7/1986 | McCoy | |
| 4,603,694 A | 8/1986 | Wheeler | |
| 4,605,454 A | 8/1986 | Sayovitz et al. | |
| 4,607,185 A | 8/1986 | Elbert et al. | |
| 4,609,368 A | 9/1986 | Dotson, Jr. | |
| 4,620,545 A | 11/1986 | Shene et al. | |
| 4,633,119 A | 12/1986 | Thompson | |
| 4,634,420 A | 1/1987 | Spinosa et al. | 604/22 |
| 4,642,509 A | 2/1987 | Kumada | |
| 4,643,717 A | 2/1987 | Cook et al. | |
| 4,647,336 A | 3/1987 | Coenen et al. | |
| 4,647,871 A | 3/1987 | Turner, Jr. | |
| 4,651,043 A | 3/1987 | Harris et al. | |
| 4,652,785 A | 3/1987 | Gabriel et al. | |
| 4,652,786 A | 3/1987 | Mishiro | |
| 4,655,104 A | 4/1987 | Blattner | |
| 4,663,556 A | 5/1987 | Kumada | |
| 4,676,975 A | 6/1987 | McGary et al. | |
| 4,678,993 A | 7/1987 | Vinnemann et al. | |
| 4,688,454 A | 8/1987 | Scull | |
| 4,690,722 A | 9/1987 | Flood | |
| 4,692,139 A | 9/1987 | Stiles | |
| 4,696,299 A | 9/1987 | Shene et al. | |
| 4,702,236 A | 10/1987 | Tarabichy et al. | |
| 4,704,131 A | 11/1987 | Noishiki et al. | |
| 4,704,573 A | 11/1987 | Turner, Jr. | |
| 4,708,127 A | 11/1987 | Abdelghani | |
| 4,713,132 A | 12/1987 | Abel et al. | |
| 4,715,078 A | 12/1987 | Howard et al. | |

| Patent No. | Date | Inventor | Class |
|---|---|---|---|
| 4,718,907 A | 1/1988 | Karwoski et al. | |
| 4,730,614 A | 3/1988 | Lacruche et al. | |
| 4,732,152 A | 3/1988 | Wallsten et al. | |
| 4,732,156 A | 3/1988 | Nakamura | |
| 4,735,625 A | 4/1988 | Davidson | |
| 4,738,666 A | 4/1988 | Fuqua | |
| 4,738,667 A | 4/1988 | Galloway | |
| 4,747,820 A | 5/1988 | Hornlein et al. | |
| 4,748,985 A | 6/1988 | Nagasaki | |
| 4,748,986 A | 6/1988 | Morrison et al. | |
| 4,749,437 A | 6/1988 | Welter | |
| 4,750,488 A | 6/1988 | Wuchinich et al. | |
| 4,750,902 A | 6/1988 | Wuchinich et al. | |
| 4,751,916 A | 6/1988 | Bory | |
| 4,756,304 A | 7/1988 | Watanabe | |
| 4,756,309 A | 7/1988 | Sachse et al. | |
| 4,758,222 A | 7/1988 | McCoy | |
| 4,758,293 A | 7/1988 | Samida | |
| 4,762,668 A | 8/1988 | Loose et al. | |
| 4,770,730 A | 9/1988 | Abe | |
| 4,771,202 A | 9/1988 | Takahashi | |
| 4,771,782 A | 9/1988 | Millar | |
| 4,791,915 A | 12/1988 | Barsotti et al. | |
| 4,794,912 A | 1/1989 | Lia | |
| 4,823,723 A | 4/1989 | Brooks | |
| 4,823,783 A | 4/1989 | Willhite, Jr. et al. | |
| 4,825,851 A | 5/1989 | Cocks et al. | |
| 4,828,052 A | 5/1989 | Duran et al. | |
| 4,830,002 A | 5/1989 | Semm | |
| 4,834,102 A | 5/1989 | Schwarzchild et al. | |
| 4,838,853 A | 6/1989 | Parisi | 604/22 |
| 4,838,859 A | 6/1989 | Strassmann | |
| 4,844,081 A | 7/1989 | Northeved et al. | |
| 4,846,161 A | 7/1989 | Roger | |
| 4,846,174 A | 7/1989 | Willard et al. | |
| 4,846,790 A | 7/1989 | Hornlein et al. | |
| 4,850,358 A | 7/1989 | Millar | |
| 4,862,573 A | 9/1989 | Kelson et al. | |
| 4,866,491 A | 9/1989 | Solomon et al. | |
| 4,867,141 A | 9/1989 | Nakada et al. | 601/4 |
| 4,870,953 A * | 10/1989 | DonMicheal et al. | 606/128 |
| 4,872,333 A | 10/1989 | Burnand | |
| 4,873,969 A | 10/1989 | Huebsch | |
| 4,877,037 A | 10/1989 | Ko et al. | |
| 4,880,011 A | 11/1989 | Imade et al. | |
| 4,881,761 A | 11/1989 | Hornlein et al. | |
| 4,882,777 A | 11/1989 | Narula | |
| 4,885,499 A | 12/1989 | Ueha et al. | |
| 4,886,060 A | 12/1989 | Wiksell | |
| 4,886,491 A | 12/1989 | Parisi et al. | 304/22 |
| 4,892,089 A | 1/1990 | Cocks et al. | |
| 4,904,391 A | 2/1990 | Freeman | |
| 4,907,572 A | 3/1990 | Borodulin et al. | |
| 4,909,789 A | 3/1990 | Taguchi et al. | |
| 4,917,104 A | 4/1990 | Rebell | |
| 4,920,954 A | 5/1990 | Alliger et al. | 128/24 A |
| 4,922,902 A | 5/1990 | Wuchinich et al. | 604/22 |
| 4,924,863 A | 5/1990 | Sterzer | |
| 4,931,047 A | 6/1990 | Broadwin et al. | 604/22 |
| 4,931,049 A | 6/1990 | Klimas | |
| 4,936,281 A | 6/1990 | Stasz | |
| 4,960,410 A | 10/1990 | Pinchuk | |
| 4,961,424 A | 10/1990 | Kubota et al. | 128/24 A |
| 4,962,755 A | 10/1990 | King et al. | 601/2 |
| 4,963,151 A | 10/1990 | Ducheyne et al. | |
| 4,966,131 A | 10/1990 | Houghton et al. | |
| 4,966,148 A | 10/1990 | Millar | |
| 4,974,581 A | 12/1990 | Wiksell | |
| 4,978,333 A | 12/1990 | Broadwin et al. | |
| 4,979,952 A | 12/1990 | Kubota et al. | |
| 4,986,808 A | 1/1991 | Broadwin et al. | |
| 4,989,583 A | 2/1991 | Hood | 128/24 A |
| 4,989,588 A | 2/1991 | Kubota et al. | |
| 5,003,965 A | 4/1991 | Talish et al. | |
| 5,003,990 A | 4/1991 | Osypka | |
| 5,015,221 A | 5/1991 | Smith | |
| 5,015,227 A | 5/1991 | Broadwin et al. | 604/22 |
| 5,017,379 A | 5/1991 | Lemelson | |
| 5,019,083 A | 5/1991 | Klapper et al. | |
| 5,024,234 A | 6/1991 | Leary et al. | |
| 5,026,387 A | 6/1991 | Thomas | 606/169 |
| 5,027,792 A | 7/1991 | Meyer | |
| 5,040,548 A | 8/1991 | Yock | |
| 5,045,054 A | 9/1991 | Hood et al. | |
| 5,046,497 A | 9/1991 | Millar | |
| 5,049,157 A | 9/1991 | Mittelmeier et al. | |
| 5,054,492 A | 10/1991 | Scribner et al. | |
| 5,055,101 A | 10/1991 | McCoy | |
| 5,057,106 A | 10/1991 | Kasevich et al. | |
| 5,057,119 A | 10/1991 | Clark et al. | 606/169 |
| 5,057,182 A | 10/1991 | Wuchinich | 156/580.1 |
| 5,058,570 A | 10/1991 | Idemoto et al. | |
| 5,059,210 A | 10/1991 | Clark et al. | 606/169 |
| 5,061,273 A | 10/1991 | Yock | |
| 5,062,827 A | 11/1991 | Wiksell | 604/22 |
| 5,064,765 A | 11/1991 | Karasikov et al. | |
| 5,069,664 A | 12/1991 | Guess et al. | |
| 5,076,276 A | 12/1991 | Sakurai et al. | |
| 5,102,403 A | 4/1992 | Alt | |
| 5,106,741 A | 4/1992 | Marotti et al. | |
| 5,108,238 A | 4/1992 | Ewing | |
| 5,109,830 A | 5/1992 | Cho | |
| 5,112,300 A | 5/1992 | Ureche | 604/22 |
| 5,116,343 A | 5/1992 | Ams et al. | 606/128 |
| 5,122,122 A | 6/1992 | Allgood | |
| 5,123,903 A | 6/1992 | Quaid et al. | |
| 5,127,405 A | 7/1992 | Alcala et al. | |
| 5,129,914 A | 7/1992 | Choi | |
| 5,139,496 A | 8/1992 | Hed | |
| 5,139,509 A | 8/1992 | Fischer et al. | |
| 5,147,316 A | 9/1992 | Castillenti | |
| 5,151,085 A | 9/1992 | Sakurai et al. | |
| 5,151,099 A | 9/1992 | Young et al. | |
| 5,152,200 A | 10/1992 | Kaplan | |
| 5,152,748 A | 10/1992 | Chastagner | |
| 5,156,143 A | 10/1992 | Bocquet et al. | |
| 5,163,421 A | 11/1992 | Bernstein et al. | 128/24 |
| 5,167,619 A | 12/1992 | Wuchinich | 604/22 |
| 5,169,386 A | 12/1992 | Becker et al. | |
| 5,171,387 A | 12/1992 | Wuchinich | 156/73.3 |
| 5,175,492 A | 12/1992 | Wong et al. | |
| 5,176,141 A | 1/1993 | Bom et al. | |
| 5,176,677 A | 1/1993 | Wuchinich | 604/356 |
| 5,180,363 A | 1/1993 | Idemoto et al. | 202/32 |
| 5,190,517 A | 3/1993 | Zieve et al. | 604/22 |
| 5,193,525 A | 3/1993 | Silverstein et al. | |
| 5,195,955 A | 3/1993 | Don Michael | |
| 5,201,315 A | 4/1993 | Griffith | |
| 5,201,316 A | 4/1993 | Pomeranz et al. | |
| 5,203,338 A | 4/1993 | Jang | |
| 5,209,719 A | 5/1993 | Baruch et al. | |
| 5,217,465 A | 6/1993 | Steppe | |
| 5,221,282 A | 6/1993 | Wuchinich | 606/99 |
| 5,222,937 A | 6/1993 | Kagawa | |
| 5,222,974 A | 6/1993 | Kensey et al. | |
| 5,231,080 A | 7/1993 | Scholkens | |
| 5,231,994 A | 8/1993 | Harmjanz | |
| 5,232,451 A | 8/1993 | Freitas et al. | |
| 5,235,964 A | 8/1993 | Abenaim | |
| 5,240,437 A | 8/1993 | Christian | |
| 5,243,997 A | 9/1993 | Uflacker et al. | 600/565 |
| 5,248,296 A | 9/1993 | Alliger | |
| 5,249,580 A | 10/1993 | Griffith | |
| 5,255,551 A | 10/1993 | Vetter | |
| 5,255,669 A | 10/1993 | Kubota et al. | |
| 5,261,805 A | 11/1993 | Gates | |

| Patent No. | Date | Inventor | Class |
|---|---|---|---|
| 5,261,877 A | 11/1993 | Fine et al. | |
| 5,263,928 A | 11/1993 | Trauthen et al. | |
| 5,263,932 A | 11/1993 | Jang | |
| 5,267,954 A | 12/1993 | Nita | 604/22 |
| 5,267,958 A | 12/1993 | Buchbinder et al. | |
| 5,267,982 A | 12/1993 | Sylvanowicz | |
| 5,269,297 A | 12/1993 | Weng et al. | 128/24 AA |
| 5,271,735 A | 12/1993 | Greenfield et al. | 604/266 |
| 5,274,297 A | 12/1993 | Hermann et al. | |
| 5,285,795 A | 2/1994 | Ryan et al. | |
| 5,287,775 A | 2/1994 | Moore | |
| 5,290,229 A | 3/1994 | Paskar | |
| 5,300,021 A | 4/1994 | Wuchinich | 604/22 |
| 5,300,032 A | 4/1994 | Hibbs et al. | |
| 5,300,085 A | 4/1994 | Yock | |
| 5,304,115 A | 4/1994 | Pflueger et al. | 604/22 |
| 5,304,131 A | 4/1994 | Paskar | |
| 5,304,199 A | 4/1994 | Myers | |
| 5,306,261 A | 4/1994 | Alliger et al. | |
| 5,307,816 A | 5/1994 | Hashimoto et al. | |
| 5,311,858 A | 5/1994 | Adair | |
| 5,312,328 A | 5/1994 | Nita et al. | 604/22 |
| 5,312,329 A | 5/1994 | Beaty et al. | 604/22 |
| 5,312,427 A | 5/1994 | Shturman | |
| 5,315,996 A | 5/1994 | Lundquist | |
| 5,318,528 A | 6/1994 | Heaven et al. | |
| 5,319,278 A | 6/1994 | Myohga et al. | |
| 5,323,902 A | 6/1994 | Palmer et al. | |
| 5,324,255 A | 6/1994 | Passafaro et al. | |
| 5,324,299 A | 6/1994 | Davison et al. | 606/167 |
| 5,325,698 A | 7/1994 | Nagpal et al. | |
| 5,326,342 A | 7/1994 | Pflueger et al. | |
| 5,329,927 A | 7/1994 | Gardineer et al. | |
| 5,330,444 A | 7/1994 | Webler et al. | |
| 5,330,482 A | 7/1994 | Gibbs et al. | |
| 5,330,497 A | 7/1994 | Freitas et al. | |
| 5,331,242 A | 7/1994 | Petri | |
| 5,334,160 A | 8/1994 | Ellis | |
| 5,334,167 A | 8/1994 | Cocanower | |
| 5,334,183 A | 8/1994 | Wuchinich | 606/46 |
| 5,336,184 A | 8/1994 | Teirstein | |
| 5,336,234 A | 8/1994 | Vigil et al. | |
| 5,336,699 A | 8/1994 | Cooke et al. | |
| 5,342,292 A | 8/1994 | Nita et al. | 604/22 |
| 5,344,395 A | 9/1994 | Whalen et al. | |
| 5,350,395 A | 9/1994 | Yock | |
| 5,351,679 A | 10/1994 | Mayzels et al. | |
| 5,353,798 A | 10/1994 | Sieben | |
| 5,356,385 A | 10/1994 | Latini | |
| 5,356,421 A | 10/1994 | Castro | |
| 5,358,505 A | 10/1994 | Wuchinich | 606/99 |
| 5,362,309 A | 11/1994 | Carter | |
| 5,366,490 A | 11/1994 | Edwards et al. | 607/99 |
| 5,366,899 A | 11/1994 | Shabalin et al. | |
| 5,368,557 A | 11/1994 | Nita et al. | |
| 5,368,558 A | 11/1994 | Nita | 604/22 |
| 5,370,602 A | 12/1994 | Kepley | |
| 5,380,273 A * | 1/1995 | Dubrul et al. | 604/22 |
| 5,380,274 A | 1/1995 | Nita | 604/22 |
| 5,382,228 A | 1/1995 | Nita et al. | 604/22 |
| 5,385,372 A | 1/1995 | Utterberg | |
| 5,387,190 A | 2/1995 | Gotanda et al. | |
| 5,387,197 A | 2/1995 | Smith et al. | |
| 5,388,569 A | 2/1995 | Kepley | |
| 5,390,678 A | 2/1995 | Gesswein et al. | |
| 5,391,144 A | 2/1995 | Sakurai et al. | |
| 5,396,902 A | 3/1995 | Brennen et al. | |
| 5,397,293 A | 3/1995 | Alliger et al. | 601/2 |
| 5,397,301 A | 3/1995 | Pflueger et al. | 604/22 |
| 5,402,799 A | 4/1995 | Colon et al. | |
| 5,403,324 A | 4/1995 | Ciervo et al. | |
| 5,405,318 A | 4/1995 | Nita | 604/22 |
| 5,405,341 A | 4/1995 | Martin | |
| 5,406,503 A | 4/1995 | Williams, Jr. et al. | |
| 5,409,112 A | 4/1995 | Sagstetter | |
| 5,417,654 A | 5/1995 | Kelman | 604/22 |
| 5,417,672 A | 5/1995 | Nita et al. | 604/533 |
| 5,419,761 A | 5/1995 | Narayanan et al. | 604/22 |
| 5,421,338 A | 6/1995 | Crowley et al. | |
| 5,421,829 A | 6/1995 | Olichney et al. | |
| 5,423,797 A | 6/1995 | Adrian et al. | |
| 5,423,838 A | 6/1995 | Willard | |
| 5,425,704 A | 6/1995 | Sakurai et al. | |
| 5,427,118 A | 6/1995 | Nita et al. | 128/772 |
| 5,429,136 A | 7/1995 | Milo et al. | |
| 5,431,664 A | 7/1995 | Ureche et al. | |
| 5,434,827 A | 7/1995 | Bolorforosh | |
| 5,443,443 A | 8/1995 | Shiber | |
| 5,443,456 A | 8/1995 | Alliger et al. | |
| 5,443,457 A | 8/1995 | Ginn et al. | |
| 5,443,468 A | 8/1995 | Johnson | |
| 5,445,617 A | 8/1995 | Yoon | |
| 5,447,509 A | 9/1995 | Mills et al. | 606/1 |
| 5,449,369 A | 9/1995 | Imran | |
| 5,451,233 A | 9/1995 | Yock | |
| 5,452,611 A | 9/1995 | Jones et al. | |
| 5,454,373 A | 10/1995 | Koger et al. | |
| 5,458,584 A | 10/1995 | Ginn et al. | |
| 5,458,612 A | 10/1995 | Chin | 606/192 |
| 5,460,595 A | 10/1995 | Hall et al. | |
| 5,462,530 A | 10/1995 | Jang | |
| 5,464,016 A | 11/1995 | Nicholas et al. | |
| 5,464,409 A | 11/1995 | Mohajer | |
| 5,464,438 A | 11/1995 | Menaker | |
| 5,467,674 A | 11/1995 | Thorn | |
| 5,469,853 A | 11/1995 | Law et al. | 128/662.06 |
| 5,470,322 A | 11/1995 | Horzewski et al. | |
| 5,472,441 A | 12/1995 | Edwards et al. | 606/41 |
| 5,474,075 A | 12/1995 | Goldberg et al. | |
| 5,474,530 A | 12/1995 | Passafaro et al. | |
| 5,474,531 A | 12/1995 | Carter | |
| 5,478,353 A | 12/1995 | Yoon | |
| 5,478,558 A | 12/1995 | Eibl et al. | |
| 5,484,398 A | 1/1996 | Stoddard | 604/22 |
| 5,492,001 A | 2/1996 | Sasaki et al. | |
| 5,498,236 A | 3/1996 | Dubrul et al. | 604/22 |
| 5,501,227 A | 3/1996 | Yock | |
| 5,505,714 A | 4/1996 | Dassa et al. | |
| 5,507,738 A | 4/1996 | Ciervo | |
| 5,512,037 A | 4/1996 | Russell et al. | |
| 5,516,043 A | 5/1996 | Manna et al. | 239/102.2 |
| 5,524,620 A | 6/1996 | Rosenschein | |
| 5,524,635 A | 6/1996 | Uflacker et al. | |
| 5,527,273 A | 6/1996 | Manna et al. | |
| 5,527,279 A | 6/1996 | Imran | |
| 5,531,664 A | 7/1996 | Adachi et al. | |
| 5,536,250 A | 7/1996 | Klein et al. | |
| 5,540,656 A | 7/1996 | Pflueger et al. | |
| 5,542,917 A | 8/1996 | Nita et al. | |
| 5,549,563 A | 8/1996 | Kronner | |
| 5,549,576 A | 8/1996 | Patterson et al. | |
| 5,562,620 A | 10/1996 | Klein et al. | |
| 5,569,276 A | 10/1996 | Jang et al. | |
| 5,571,014 A | 11/1996 | Gregory, Jr. et al. | |
| 5,571,085 A | 11/1996 | Accisano, III | |
| 5,575,772 A | 11/1996 | Lennox | |
| 5,580,962 A | 12/1996 | Eibl et al. | |
| 5,582,588 A | 12/1996 | Sakurai et al. | |
| 5,588,432 A | 12/1996 | Crowley | |
| 5,590,653 A | 1/1997 | Aida et al. | |
| 5,593,394 A | 1/1997 | Kanesaka et al. | |
| 5,599,326 A | 2/1997 | Carter | |
| 5,603,445 A | 2/1997 | Hill et al. | 228/4.5 |
| 5,607,404 A | 3/1997 | Khairkhahan | |
| 5,607,440 A | 3/1997 | Danks et al. | |
| 5,611,807 A | 3/1997 | O'Boyle | |

| | | | | | | |
|---|---|---|---|---|---|---|
| 5,622,170 A | 4/1997 | Schulz | | 5,897,557 A | 4/1999 | Chin et al. |
| 5,628,743 A | 5/1997 | Cimino ........................ 606/1 | | 5,897,569 A | 4/1999 | Kellogg et al. |
| 5,630,427 A | 5/1997 | Hastings | | 5,902,289 A | 5/1999 | Swartz et al. |
| 5,630,797 A | 5/1997 | Diedrich et al. | | 5,904,670 A | 5/1999 | Schreiner |
| 5,630,837 A | 5/1997 | Crowley ........................ 601/2 | | 5,906,628 A | 5/1999 | Miyawaki et al. |
| 5,647,846 A | 7/1997 | Berg et al. | | 5,908,381 A | 6/1999 | Aznoian et al. |
| 5,651,364 A | 7/1997 | Yock | | 5,910,129 A | 6/1999 | Koblish et al. |
| 5,651,776 A | 7/1997 | Appling et al. | | 5,916,192 A | 6/1999 | Nita et al. |
| 5,662,620 A | 9/1997 | Lieber et al. | | 5,916,210 A | 6/1999 | Winston |
| 5,666,970 A | 9/1997 | Smith | | 5,919,163 A | 7/1999 | Glickman |
| 5,669,881 A | 9/1997 | Dunshee | | 5,919,174 A | 7/1999 | Hanson |
| 5,672,172 A | 9/1997 | Zupkas ........................ 606/20 | | 5,920,395 A | 7/1999 | Schulz |
| 5,676,011 A | 10/1997 | Allison | | 5,921,915 A | 7/1999 | Aznoian et al. |
| 5,676,649 A | 10/1997 | Boukhny et al. ............... 604/22 | | 5,925,016 A | 7/1999 | Chornenky et al. |
| 5,681,296 A | 10/1997 | Ishida | | 5,928,218 A | 7/1999 | Gelbfish |
| 5,685,312 A | 11/1997 | Yock | | 5,931,805 A | 8/1999 | Brisken ........................ 604/22 |
| 5,687,474 A | 11/1997 | Hamzehdoost et al. | | 5,935,096 A | 8/1999 | Barrett ........................ 604/22 |
| 5,688,235 A | 11/1997 | Sakurai et al. | | 5,935,142 A | 8/1999 | Hood ........................ 606/169 |
| 5,690,611 A | 11/1997 | Swartz et al. | | 5,935,143 A | 8/1999 | Hood |
| 5,693,029 A | 12/1997 | Leonhardt | | 5,944,687 A | 8/1999 | Benett et al. |
| 5,704,787 A | 1/1998 | Hickok et al. | | 5,951,480 A | 9/1999 | White et al. |
| 5,707,359 A | 1/1998 | Bufalini | | 5,951,539 A | 9/1999 | Nita et al. |
| 5,709,120 A | 1/1998 | Shilling | | 5,951,583 A | 9/1999 | Jensen et al. |
| 5,713,363 A | 2/1998 | Seward et al. | | 5,957,882 A | 9/1999 | Nita et al. ........................ 604/22 |
| 5,713,848 A | 2/1998 | Dubrul et al. ................ 604/22 | | 5,961,444 A | 10/1999 | Thompson |
| 5,715,825 A | 2/1998 | Crowley | | 5,964,756 A | 10/1999 | McGaffigan et al. .......... 606/41 |
| 5,720,300 A | 2/1998 | Fagan et al. | | 5,971,949 A | 10/1999 | Levin et al. |
| 5,720,710 A | 2/1998 | Tachibana et al. ............... 601/2 | | 5,971,960 A | 10/1999 | Flom et al. |
| 5,722,627 A | 3/1998 | Hoshino | | 5,971,983 A | 10/1999 | Lesh |
| 5,725,494 A | 3/1998 | Brisken ........................ 604/22 | | 5,974,884 A | 11/1999 | Sano et al. |
| 5,728,062 A | 3/1998 | Brisken ........................ 604/22 | | 5,976,093 A | 11/1999 | Jang |
| 5,735,811 A | 4/1998 | Brisken ........................ 604/22 | | 5,980,563 A | 11/1999 | Tu et al. |
| 5,741,225 A | 4/1998 | Lax et al. ...................... 604/22 | | 5,981,444 A | 11/1999 | Sawada et al. |
| 5,749,889 A | 5/1998 | Bacich et al. | | 5,984,882 A | 11/1999 | Rosenschein et al. |
| 5,749,914 A | 5/1998 | Janssen | | 5,984,950 A | 11/1999 | Cragg et al. |
| 5,752,932 A | 5/1998 | Ellis et al. | | 5,987,349 A | 11/1999 | Schulz |
| 5,758,420 A | 6/1998 | Schmidt et al. | | 5,989,208 A | 11/1999 | Nita ........................ 604/22 |
| 5,765,418 A | 6/1998 | Rosenberg | | 5,989,209 A | 11/1999 | Barrett ........................ 604/22 |
| 5,769,868 A | 6/1998 | Yock | | 5,989,274 A | 11/1999 | Davison et al. ............. 606/169 |
| 5,772,627 A | 6/1998 | Acosta et al. ................ 604/22 | | 5,989,280 A * | 11/1999 | Euteneuer et al. ............ 623/1.1 |
| 5,775,328 A | 7/1998 | Lowe et al. | | 5,993,408 A | 11/1999 | Zaleski |
| 5,776,065 A | 7/1998 | Mehmanpazir et al. | | 5,997,497 A | 12/1999 | Nita et al. ........................ 604/22 |
| 5,782,861 A | 7/1998 | Cragg et al. | | 5,997,523 A | 12/1999 | Jang |
| 5,797,920 A | 8/1998 | Kim | | 6,001,355 A | 12/1999 | Dowdle |
| 5,803,083 A | 9/1998 | Buck et al. | | 6,004,269 A | 12/1999 | Crowley et al. |
| 5,810,860 A | 9/1998 | Adrian | | 6,007,514 A | 12/1999 | Nita |
| 5,813,998 A | 9/1998 | Dias | | 6,010,476 A | 1/2000 | Saadat |
| 5,824,042 A | 10/1998 | Lombardi et al. | | 6,010,498 A | 1/2000 | Guglielmi |
| 5,827,203 A | 10/1998 | Nita ........................ 601/2 | | 6,017,340 A | 1/2000 | Cassidy et al. |
| 5,827,229 A | 10/1998 | Auth et al. | | 6,017,354 A | 1/2000 | Culp et al. |
| 5,830,125 A | 11/1998 | Scribner et al. | | 6,017,359 A | 1/2000 | Gershony et al. |
| 5,830,127 A | 11/1998 | DeCastro | | 6,019,777 A | 2/2000 | Mackenzie |
| 5,830,195 A | 11/1998 | Peters et al. | | 6,021,694 A | 2/2000 | Beger |
| 5,833,644 A | 11/1998 | Zadno-Azizi et al. | | 6,022,336 A | 2/2000 | Zadno-Azizi et al. |
| 5,833,650 A | 11/1998 | Imran | | 6,022,369 A | 2/2000 | Jacobsen et al. |
| 5,836,306 A | 11/1998 | Duane et al. | | 6,024,718 A * | 2/2000 | Chen et al. .................... 604/22 |
| 5,836,896 A | 11/1998 | Rosenschein ................... 601/2 | | 6,027,515 A | 2/2000 | Cimino |
| 5,836,897 A | 11/1998 | Sakuri et al. ................... 601/2 | | 6,032,078 A | 2/2000 | Rudie ........................ 607/101 |
| 5,840,027 A | 11/1998 | Swartz et al. | | 6,033,375 A | 3/2000 | Brumbach .................... 604/22 |
| 5,840,031 A | 11/1998 | Crowley | | 6,033,411 A | 3/2000 | Preissman |
| 5,840,151 A | 11/1998 | Munsch | | 6,036,648 A * | 3/2000 | White et al. ................. 600/459 |
| 5,843,017 A | 12/1998 | Yoon ........................ 604/22 | | 6,036,671 A | 3/2000 | Frey |
| 5,846,218 A | 12/1998 | Brisken et al. ................ 604/22 | | 6,036,697 A | 3/2000 | DiCaprio |
| 5,849,009 A | 12/1998 | Bernaz | | 6,036,715 A | 3/2000 | Yock |
| 5,861,023 A | 1/1999 | Vachon | | 6,039,693 A | 3/2000 | Seward et al. |
| 5,868,773 A | 2/1999 | Danks et al. | | 6,039,762 A | 3/2000 | McKay |
| 5,868,778 A | 2/1999 | Gershony et al. | | 6,045,527 A | 4/2000 | Appelbaum et al. |
| 5,875,782 A | 3/1999 | Ferrari et al. | | 6,048,329 A | 4/2000 | Thompson et al. |
| 5,882,347 A | 3/1999 | Mouris-Laan et al. | | 6,050,949 A | 4/2000 | White et al. |
| 5,890,406 A | 4/1999 | Thorn | | 6,051,772 A | 4/2000 | Cameron et al. |
| 5,891,149 A | 4/1999 | Young et al. .................... 606/80 | | 6,053,904 A | 4/2000 | Scribner et al. |
| 5,895,370 A | 4/1999 | Edwards et al. ............... 604/22 | | RE36,693 E | 5/2000 | Reich |
| 5,895,997 A | 4/1999 | Puskas et al. | | 6,056,722 A | 5/2000 | Jayaraman |

| | | | |
|---|---|---|---|
| 6,057,798 A | 5/2000 | Burrier et al. | |
| 6,059,789 A | 5/2000 | Dinger et al. | |
| 6,062,001 A | 5/2000 | Kunik | |
| 6,062,059 A | 5/2000 | Feldcamp | |
| 6,068,610 A | 5/2000 | Ellis et al. | |
| 6,077,285 A | 6/2000 | Boukhny | 606/169 |
| 6,083,191 A | 7/2000 | Rose | |
| 6,083,501 A | 7/2000 | Miyata et al. | |
| 6,090,118 A | 7/2000 | McGuckin, Jr. | |
| 6,099,464 A | 8/2000 | Shimizu et al. | |
| 6,106,475 A | 8/2000 | Lowe et al. | |
| 6,106,538 A | 8/2000 | Shiber | |
| 6,107,161 A | 8/2000 | Kitaguro et al. | |
| 6,110,142 A | 8/2000 | Pinchuk et al. | |
| 6,110,176 A | 8/2000 | Shapira | |
| 6,113,558 A | 9/2000 | Rosenschein et al. | |
| 6,113,570 A | 9/2000 | Siegel et al. | |
| 6,113,580 A | 9/2000 | Dolisi | |
| 6,123,718 A | 9/2000 | Tu et al. | |
| 6,124,150 A | 9/2000 | Corisis | |
| 6,124,546 A | 9/2000 | Hayward et al. | |
| 6,124,634 A | 9/2000 | Akram et al. | |
| 6,129,672 A | 10/2000 | Seward et al. | |
| 6,146,380 A | 11/2000 | Racz et al. | |
| 6,146,381 A | 11/2000 | Bowe et al. | |
| 6,156,018 A | 12/2000 | Hassett | |
| 6,159,195 A | 12/2000 | Ha et al. | |
| 6,162,053 A | 12/2000 | Hollander | |
| 6,165,197 A | 12/2000 | Yock | |
| 6,190,353 B1 | 2/2001 | Makower et al. | |
| 6,193,683 B1 | 2/2001 | Ludin et al. | |
| 6,200,269 B1 | 3/2001 | Lin et al. | |
| 6,200,315 B1 | 3/2001 | Gaiser et al. | |
| 6,203,516 B1 | 3/2001 | Kepley | |
| 6,203,568 B1 | 3/2001 | Lombardi et al. | |
| 6,224,565 B1 | 5/2001 | Cimino | 604/22 |
| 6,228,046 B1 | 5/2001 | Brisken | 604/22 |
| 6,231,514 B1 | 5/2001 | Lowe et al. | |
| 6,231,518 B1 | 5/2001 | Grabek et al. | |
| 6,234,971 B1 | 5/2001 | Jang | |
| 6,235,000 B1 | 5/2001 | Milo et al. | |
| 6,241,703 B1 | 6/2001 | Levin et al. | |
| 6,245,095 B1 | 6/2001 | Dobak, III et al. | |
| 6,247,592 B1 | 6/2001 | Racicot et al. | |
| 6,258,798 B1 | 7/2001 | Wallentin | |
| 6,262,062 B1 | 7/2001 | Clemens | |
| 6,270,460 B1 | 8/2001 | McCartan et al. | |
| 6,277,084 B1 | 8/2001 | Abele et al. | |
| 6,279,743 B1 | 8/2001 | Ballard et al. | |
| 6,280,413 B1 | 8/2001 | Clark et al. | |
| 6,283,951 B1 | 9/2001 | Flaherty et al. | |
| 6,287,271 B1 | 9/2001 | Dubrul et al. | 604/22 |
| 6,287,272 B1 | 9/2001 | Brisken et al. | |
| 6,290,662 B1 | 9/2001 | Morris et al. | |
| 6,290,673 B1 | 9/2001 | Shanley | |
| 6,293,725 B1 | 9/2001 | Winkvist | |
| 6,296,658 B1 | 10/2001 | Gershony et al. | |
| 6,303,635 B1 | 10/2001 | Kawai et al. | |
| 6,306,097 B1 | 10/2001 | Park et al. | |
| 6,307,156 B1 | 10/2001 | Avellanet | |
| 6,309,379 B1 | 10/2001 | Willard et al. | |
| 6,312,406 B1 | 11/2001 | Jayaraman | |
| 6,322,541 B2 | 11/2001 | West et al. | |
| 6,329,778 B1 | 12/2001 | Culp et al. | |
| 6,346,091 B1 | 2/2002 | Jacobsen et al. | |
| 6,348,039 B1 | 2/2002 | Flachman et al. | |
| 6,358,252 B1 | 3/2002 | Shapira | |
| 6,364,840 B1 | 4/2002 | Crowley | 600/463 |
| 6,364,841 B1 | 4/2002 | White et al. | |
| 6,368,611 B1 | 4/2002 | Whitbourne et al. | |
| 6,376,513 B1 | 4/2002 | Akahane et al. | |
| 6,383,151 B1 | 5/2002 | Diederich et al. | |
| 6,391,042 B1 | 5/2002 | Cimino | |
| 6,396,293 B1 | 5/2002 | Vinther et al. | |
| 6,398,776 B1 | 6/2002 | Sekino et al. | |
| 6,398,792 B1 | 6/2002 | O'Connor | |
| 6,410,560 B1 | 6/2002 | Akahane et al. | |
| 6,416,511 B1 | 7/2002 | Lesh et al. | |
| 6,416,530 B2 | 7/2002 | DeVries et al. | |
| 6,416,737 B1 | 7/2002 | Manolagas et al. | |
| 6,419,644 B1 | 7/2002 | White et al. | |
| 6,433,464 B2 | 8/2002 | Jones | |
| 6,440,726 B1 | 8/2002 | Resnick | |
| 6,440,947 B1 | 8/2002 | Barron et al. | |
| 6,443,903 B1 | 9/2002 | White et al. | |
| 6,450,975 B1 | 9/2002 | Brennan et al. | |
| 6,451,303 B1 | 9/2002 | Whitehouse et al. | |
| 6,454,737 B1 | 9/2002 | Nita et al. | |
| 6,454,757 B1 | 9/2002 | Nita et al. | |
| 6,457,365 B1 | 10/2002 | Stephens et al. | |
| 6,458,375 B1 | 10/2002 | Gertzman et al. | |
| 6,462,172 B1 | 10/2002 | Maclennan et al. | |
| 6,464,660 B2 | 10/2002 | Brisken et al. | |
| 6,469,419 B2 | 10/2002 | Kato et al. | |
| 6,471,656 B1 | 10/2002 | Shalman et al. | |
| 6,475,185 B1 | 11/2002 | Rauker et al. | |
| 6,478,751 B1 | 11/2002 | Krueger et al. | |
| 6,482,218 B1 | 11/2002 | Tran | |
| 6,485,481 B1 | 11/2002 | Pfeiffer | |
| 6,491,710 B2 | 12/2002 | Satake | |
| 6,491,711 B1 | 12/2002 | Durcan | |
| 6,494,883 B1 | 12/2002 | Ferree | |
| 6,494,885 B1 | 12/2002 | Dhindsa | |
| 6,494,891 B1 | 12/2002 | Cornish et al. | |
| 6,494,893 B2 | 12/2002 | Dubrul et al. | |
| 6,497,667 B1 | 12/2002 | Miller et al. | |
| 6,497,698 B1 | 12/2002 | Fonger et al. | |
| 6,503,223 B1 | 1/2003 | Sekido et al. | |
| 6,508,781 B1 | 1/2003 | Brennan et al. | |
| 6,508,782 B1 | 1/2003 | Evans et al. | |
| 6,509,348 B1 | 1/2003 | Ogletree | |
| 6,511,492 B1 | 1/2003 | Rosenbluth et al. | |
| 6,512,957 B1 | 1/2003 | Witte | |
| 6,514,210 B2 | 2/2003 | Ohara et al. | |
| 6,522,929 B2 | 2/2003 | Swing | |
| 6,524,251 B2 * | 2/2003 | Rabiner et al. | 600/439 |
| 6,527,115 B2 | 3/2003 | Rabiner et al. | |
| 6,530,923 B1 | 3/2003 | Dubrul et al. | |
| 6,544,276 B1 | 4/2003 | Azizi | |
| 6,544,279 B1 | 4/2003 | Hopkins et al. | |
| 6,544,541 B1 | 4/2003 | Zahradka | |
| 6,547,724 B1 | 4/2003 | Soble et al. | |
| 6,547,754 B1 | 4/2003 | Evans et al. | |
| 6,551,269 B2 | 4/2003 | Clemens et al. | |
| 6,551,327 B1 | 4/2003 | Dhindsa | |
| 6,551,337 B1 | 4/2003 | Rabiner et al. | |
| 6,558,334 B2 | 5/2003 | Shalman et al. | |
| 6,569,109 B2 | 5/2003 | Sakurai et al. | |
| 6,569,148 B2 | 5/2003 | Bagaoisan et al. | |
| 6,572,555 B2 | 6/2003 | White et al. | |
| 6,575,959 B1 | 6/2003 | Sarge et al. | |
| 6,575,993 B1 | 6/2003 | Yock | |
| 6,577,042 B2 | 6/2003 | Lee et al. | |
| 6,579,277 B1 | 6/2003 | Rabiner et al. | |
| 6,579,279 B1 | 6/2003 | Rabiner et al. | |
| 6,579,302 B2 | 6/2003 | Duerig et al. | |
| 6,585,657 B2 | 7/2003 | Yock | |
| 6,589,253 B1 | 7/2003 | Cornish et al. | |
| 6,592,548 B2 | 7/2003 | Jayaraman | |
| 6,596,020 B2 | 7/2003 | Vardi et al. | |
| 6,605,074 B2 | 8/2003 | Zadno-Azizi et al. | |
| 6,611,793 B1 | 8/2003 | Burnside et al. | |
| 6,615,080 B1 | 9/2003 | Unsworth et al. | |
| 6,617,760 B1 | 9/2003 | Peterson et al. | |
| 6,620,113 B2 | 9/2003 | White et al. | |
| 6,626,853 B2 | 9/2003 | White et al. | |

| | | |
|---|---|---|
| 6,626,926 B2 | 9/2003 | Friedman et al. |
| 6,629,948 B2 | 10/2003 | Rockley et al. |
| 6,645,149 B1 | 11/2003 | Smith |
| 6,645,152 B1 | 11/2003 | Jung et al. |
| 6,647,755 B2 | 11/2003 | Rabiner et al. |
| 6,648,881 B2 | 11/2003 | KenKnight et al. |
| 6,652,547 B2 | 11/2003 | Rabiner et al. .............. 606/159 |
| 6,655,386 B1 | 12/2003 | Makower et al. |
| 6,660,013 B2 | 12/2003 | Rabiner et al. |
| 6,669,665 B2 | 12/2003 | Jayaraman |
| 6,679,873 B2 | 1/2004 | Rabiner et al. |
| 6,682,556 B1 | 1/2004 | Ischinger |
| 6,689,086 B1 | 2/2004 | Nita et al. |
| 6,689,087 B2 | 2/2004 | Pal et al. |
| 6,692,460 B1 | 2/2004 | Jayaraman |
| 6,695,781 B2 | 2/2004 | Rabiner et al. |
| 6,695,782 B2 | 2/2004 | Ranucci et al. |
| 6,702,748 B1 | 3/2004 | Nita et al. |
| 6,702,750 B2 | 3/2004 | Yock |
| 6,712,766 B2 | 3/2004 | Harada |
| 6,726,698 B2 | 4/2004 | Cimino |
| D489,973 S | 5/2004 | Root et al. |
| 6,730,037 B2 | 5/2004 | Jang |
| 6,730,048 B1 | 5/2004 | Hare et al. |
| 6,733,451 B2 | 5/2004 | Rabiner et al. |
| 6,760,165 B2 | 7/2004 | Wulff et al. |
| 6,761,690 B2 | 7/2004 | Sakurai et al. |
| 6,790,204 B2 | 9/2004 | Zadno-Azizi et al. |
| 6,802,835 B2 | 10/2004 | Rabiner et al. |
| 6,840,952 B2 | 1/2005 | Saker et al. |
| 6,849,062 B2 | 2/2005 | Kantor |
| 6,855,123 B2 | 2/2005 | Nita |
| 6,855,125 B2 | 2/2005 | Shanley |
| 6,860,876 B2 | 3/2005 | Chen |
| 6,866,670 B2 | 3/2005 | Rabiner et al. |
| 6,878,106 B1 | 4/2005 | Herrmann |
| 6,887,257 B2 | 5/2005 | Salahieh et al. |
| 6,908,472 B2 | 6/2005 | Wiener et al. |
| 6,921,411 B2 | 7/2005 | Yock |
| 6,923,788 B2 | 8/2005 | Kantor |
| 6,929,632 B2 | 8/2005 | Nita et al. |
| 6,939,317 B2 | 9/2005 | Zacharias |
| 6,942,620 B2 | 9/2005 | Nita et al. |
| 6,942,677 B2 | 9/2005 | Nita et al. |
| 6,966,891 B2 | 11/2005 | Ookubo et al. |
| 6,984,220 B2 | 1/2006 | Wuchinich |
| 2001/0047166 A1 | 11/2001 | Wuchinich |
| 2002/0007130 A1 | 1/2002 | Burbank et al. |
| 2002/0016565 A1 | 2/2002 | Zadno-Azizi et al. |
| 2002/0029014 A1 | 3/2002 | Jayaraman |
| 2002/0029054 A1 | 3/2002 | Rabiner et al. |
| 2002/0055754 A1 | 5/2002 | Ranucci et al. |
| 2002/0077550 A1 | 6/2002 | Rabiner et al. |
| 2002/0077643 A1 | 6/2002 | Rabiner et al. |
| 2002/0082503 A1 | 6/2002 | Chandrasekaran et al. |
| 2002/0091407 A1 | 7/2002 | Zadno-Azizi et al. |
| 2002/0095141 A1 | 7/2002 | Belef et al. |
| 2002/0107446 A1 | 8/2002 | Rabiner et al. |
| 2003/0009125 A1 | 1/2003 | Nita et al. |
| 2003/0045835 A1 | 3/2003 | Anderson et al. |
| 2003/0045887 A1 | 3/2003 | Sakurai et al. |
| 2003/0048037 A1 | 3/2003 | Boyd |
| 2003/0074006 A1 | 4/2003 | Mowry et al. |
| 2003/0114732 A1 | 6/2003 | Webler et al. |
| 2003/0120208 A1 | 6/2003 | Houser et al. |
| 2003/0125751 A1 | 7/2003 | Griffin et al. |
| 2003/0176791 A1 | 9/2003 | Rabiner et al. |
| 2003/0181923 A1 | 9/2003 | Vardi |
| 2003/0197958 A1 | 10/2003 | Wulff et al. |
| 2003/0212331 A1 | 11/2003 | Fenton et al. |
| 2003/0225332 A1 | 12/2003 | Okada et al. |
| 2003/0236539 A1 | 12/2003 | Rabiner et al. |
| 2004/0019266 A1 | 1/2004 | Marciante et al. |
| 2004/0024393 A1 | 2/2004 | Nita et al. |
| 2004/0024402 A1 | 2/2004 | Nita |
| 2004/0039311 A1 | 2/2004 | Nita et al. |
| 2004/0039375 A1 | 2/2004 | Miyazawa |
| 2004/0059227 A1 | 3/2004 | Nita et al. |
| 2004/0059280 A1 | 3/2004 | Makower et al. |
| 2004/0068189 A1 | 4/2004 | Wilson et al. |
| 2004/0097996 A1 | 5/2004 | Rabiner et al. |
| 2004/0106866 A1 | 6/2004 | Ookubo et al. |
| 2004/0119287 A1 | 6/2004 | Williams et al. |
| 2004/0138570 A1 | 7/2004 | Nita et al. |
| 2004/0167507 A1 | 8/2004 | Nita et al. |
| 2004/0199228 A1 | 10/2004 | Wilson |
| 2004/0204670 A1 | 10/2004 | Nita et al. |
| 2004/0204729 A1 | 10/2004 | Cimino |
| 2004/0210140 A1 | 10/2004 | Rabiner et al. |
| 2004/0213866 A1 | 10/2004 | Wulff et al. |
| 2004/0243052 A1 | 12/2004 | Kauphusman et al. |
| 2005/0043629 A1 | 2/2005 | Rabiner et al. |
| 2005/0059991 A1 | 3/2005 | Shanley |
| 2005/0070794 A1 | 3/2005 | Deal et al. |
| 2005/0101870 A1 | 5/2005 | Yamaguchi et al. |
| 2005/0101906 A1 | 5/2005 | Nita |
| 2005/0113688 A1 | 5/2005 | Nita et al. |
| 2005/0119606 A1 | 6/2005 | Nita |
| 2005/0124877 A1 | 6/2005 | Nita et al. |
| 2005/0171570 A1 | 8/2005 | Yock |
| 2005/0209677 A1 | 9/2005 | Shaked |
| 2005/0240165 A1 | 10/2005 | Miki et al. |
| 2005/0245951 A1 | 11/2005 | Nita et al. |
| 2005/0277577 A1 | 12/2005 | Hunter et al. |
| 2005/0283080 A1 | 12/2005 | Nita et al. |

FOREIGN PATENT DOCUMENTS

| | | |
|---|---|---|
| CA | 2320300 | 8/1999 |
| CA | 2 362 689 | 9/2000 |
| DE | 428980 | 5/1926 |
| DE | 203 229 | 10/1983 |
| DE | 37 31 482 | 4/1988 |
| EP | 0 121 491 | 10/1984 |
| EP | 0 243 298 | 10/1987 |
| EP | 0 293 472 | 12/1988 |
| EP | 0293472 | 12/1988 |
| EP | 0 316 796 | 5/1989 |
| EP | 0 353 294 | 2/1990 |
| EP | 0 493 047 | 7/1992 |
| EP | 0 541 249 | 5/1993 |
| EP | 0 542 103 | 5/1993 |
| EP | 0541249 | 5/1993 |
| EP | 0 891 744 | 1/1999 |
| FR | 461395 | 12/1913 |
| FR | 2 614 524 | 11/1988 |
| GB | 19559 | 9/1899 |
| GB | 1 371 335 | 10/1974 |
| GB | 2 032 221 | 4/1980 |
| GB | 2 325 192 | 11/1998 |
| JP | 62-224339 | 3/1986 |
| JP | 64-027548 | 1/1989 |
| JP | 02092348 A * | 4/1990 |
| WO | WO 87/01276 | 3/1987 |
| WO | WO 89/06515 | 7/1989 |
| WO | WO 90/01300 | 2/1990 |
| WO | WO 90/10423 | 9/1990 |
| WO | WO 91/07138 | 5/1991 |
| WO | WO 92/04071 | 3/1992 |
| WO | WO 92/11815 | 7/1992 |
| WO | WO 93/16646 | 9/1993 |
| WO | WO 95/03740 | 2/1995 |
| WO | WO 96/07377 | 3/1996 |
| WO | WO 98/35721 | 8/1998 |
| WO | WO 98/55032 | 12/1998 |
| WO | WO 99/16360 | 4/1999 |

| WO | WO 99/33404 | 7/1999 |
| WO | WO 99/35982 | 7/1999 |
| WO | WO 99/39647 | 8/1999 |
| WO | WO 00/21444 | 4/2000 |
| WO | WO 00/53263 | 9/2000 |

OTHER PUBLICATIONS

PCT International Search Report for International Application No. PCT/US03/09099 dated Mar. 2, 2004.

BBI Newsletter, vol. XIII, No. 3, p. 44, Biomedical Business International, 1524 Brookhollow Drive, Santa Ana, California 92705 (1990).

Beckenbaugh, R.D. and M.S. Ilstrup, *Total Hip Arthroplasty*, J. Bone and Joint Surgery, vol. 60A, pp. 308-314 (1978).

Brochure, Endo-Urology—A Breakthrough in Ultrasonic Lithotripsy, Karl Storz Endoscopy—America, Inc. (1984).

Brochure, Instruments and Apparatus for Lithotripsy, Richard Wolf GmbH, Knittlinger, West Germany (1984).

Brochure, Percutaneous Low Pressure Universal Nephroscope, Richard Wolf, Knittlinger, West Germany (1984).

Cameron, Proximal Femoral Osteotomy in Difficult Revision Hip Surgery: How to Revise the Unrevisable, 18 Contemp. Orthopaedics 565 (1989).

Caspar, Current Development of Instrumentation for Arthroscopy, *Clinics in Sports Medicine*, 6:3 (1987), pp. 626-627.

Chaussy et al., "Transurethral Ultrasonic Ureterolithotripsy Using a Solid-Wire Probe," *Urology*, 29(5):531-532 (May 1987).

De Puy Inc., Catalog (1966).

Eisner, Physical Acoustics, 1964, pp. 353-363.

Emsinger, Ultrasonics, 1988, pp. 419-492.

Ensminger, *Ultrasonics: Fundamentals, Technology, Applications*, pp. 462-467, Marcel Dekker Inc. (1988).

Epstein et al., Surgical Management of Extensive Intramedullary Spinal Cord Astrocytoma in Children, Concepts in Pediatric Neurosurgery, 2, (1982) pp. 29-44.

Goliamina, "*Ultrasonic Surgery*", Proceedings of the Eighth Int'l. Cong. On Acoustics, London, 1974, pp. 63-69.

Gray, "Endovascular treatment of peripheral arterial disease," *Journal of the American Osteopathic Association*, 100(10):S15-S20 (Supplement to Oct. 2000).

Harris et al., A New Technique for Removal of Broken Femoral Stems in Total Hip Replacement, 63-A J. Bone & Joint Surgery 843 (1981).

Johnson, Arthroscopic Surgery: Principles and Practice (3rd Edition), Verlag Springer (1986), pp. 244-245.

Karpman et al., The Lithotriptor and Its Potential Use in the Revision of Total Hip Arthroplasty, 16 Orthopaedic Rev. 81 (1987).

Klapper and Caillouette, "*The Use of Ultrasonic Tools in Revision Arthoplasty Procedures*", 20:3 Contemporary Orthopaedics, pp. 273-279 (Mar. 1990).

Krawitt et al., Ultrasonic Aspiration of Prostate, Bladder Tumors and Stones, *Urology*, 30:6 (1987) pp. 578-580.

Lin, Posterior Lumbar Interbody Fusion Technique: Complications and Pitfalls, 193 Clinical Orthopaedics and Related Research 90 (1985).

Malloy et al., Endoscopis Ultrasonic Aspiration of the Prostate, Bladder Tumors and Stones, Journal of Urology Supplement, May 1989.

Malloy et al., Transurethral Ultrasonic Aspiration of the Prostate, A.U.A., May 1989.

McClelland et al., Atraumatic Removal of a Well-Fixed Porous Ingrowth Hip Prosthesis, 15 Orthopaedic Rev. 75 (1986).

Moreland et al., *Techniques for Removal of Prosthesis and Cement in Total Hip Revisional Surgery*, Contemporary Orthopaedics, V. 21, No. 6, pp. 595-635, 1990.

Moreland et al., The Window Technique for the Removal of Broken Femoral Stems in Total Hip Replacement, 212 Clinical Orthopaedics and Related Research 245 (1986).

Neppiras, The Pre-Stressed Piezoelectric Sandwich Transducer, 1973, pp. 295-302.

Rayleigh, The Theory of Sound, vol. 1, 1894, pp. 255-305.

Richards Mfg. Co., Orthopedic Catalog (1981).

Richmond et al., Evaluation of the Histopathology of Brain Tumor Tisue Obtained by Ultrasonic Aspiration, *Neurosurgery*, 13:4 (1983), pp. 415-419.

Rozenberg, Sources of High-Intensity Ultrasound, vol. 2, 1973, pp. 111-114.

Sahagian, Richard, "Critical Insight: Marking Devices with Radiopaque Coatings," May 1999, *Medical Device & Diagnostic Industry Magazine* (http://www.devicelink.com/mddi/archive/99/05/011.html).

Schwartz, Jr. et al., Femoral Fracture During Non-Cemented Total Hip Arthroplasty, 71-A J. Bone & Joint Surgery 1135 (1989).

Sternlieb et al., Ultrasonic Restoration of Severely Calcified Aortic Valve, *The Lancet*, Aug. 20, 1988, p. 446.

Weis, Jr., A Sonic Tool for Spinal Fusion, 8 Orthopedic Clinics of North Am. 43 (1977).

Wick et al., "Tool and Manufacturing Engineers Handbood," Fourth Edition, vol. II, Forming, Society of Manufacturing Engineers, Dearbord, Michigan, 1983-1984, pp. 13-1 through 13-2 (*spelling error?*).

Zhou et al., Effect of Press-Fit Femoral Stems on Strains in the Femur, 5 J. Arthroplasty 71 (1990).

* cited by examiner

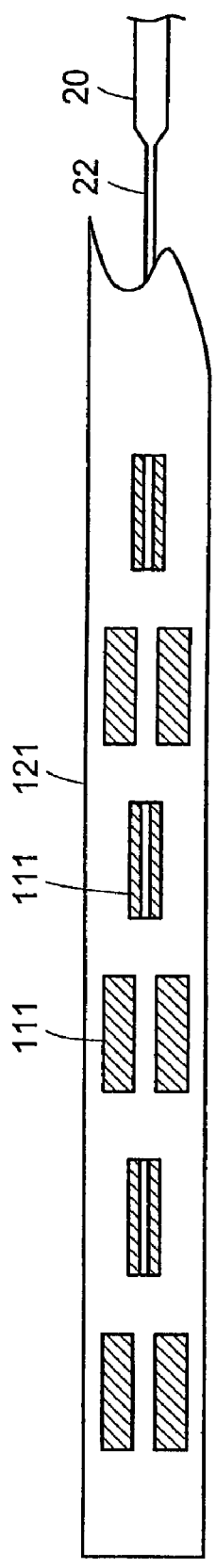
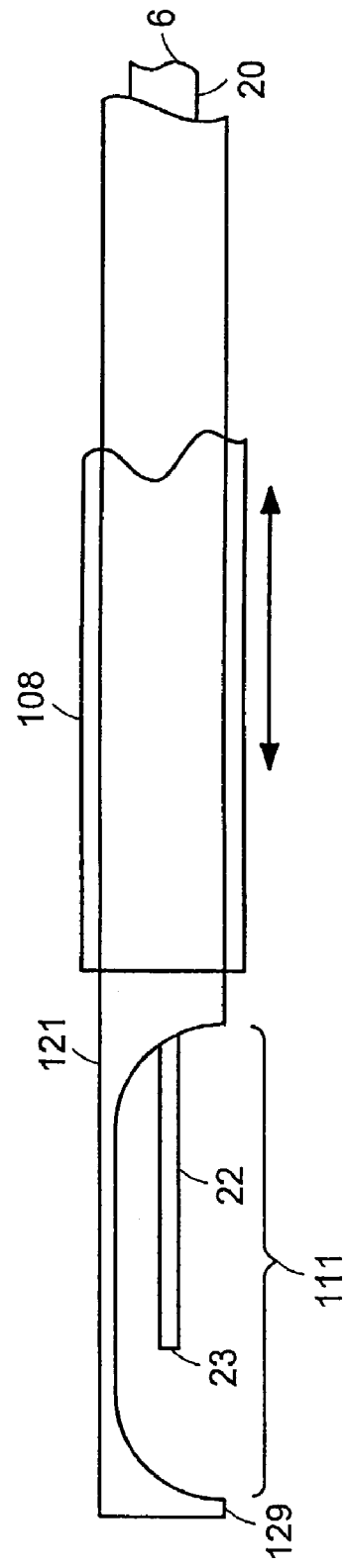
FIG. 4
FIG. 5

ULTRASONIC DEVICE FOR TISSUE ABLATION AND SHEATH FOR USE THEREWITH

FIELD OF THE INVENTION

The present invention relates generally to a shielded ultrasonic medical probe operating in a transverse mode for ablating and removing undesired tissue. In particular, the invention provides one or more acoustical sheaths for use with the probe, allowing the user to control and focus the energy emitted by the probe in a manner most suited to the desired medical procedure.

BACKGROUND OF THE INVENTION

Ultrasonic energy has been considered for tissue ablation and fragmentation of plaque and thrombosis for removal of intravascular occlusions due to atherosclerotic plaque and intravascular blood clots. Surgical devices utilizing ultrasonic probes for generation and transmission of ultrasonic energy, have been disclosed in the art (U.S. Pat. Nos. 5,112,300; 5,180,363; 4,989,583; 4,931,047; 4,922,902; and 3,805,787). Typically, the energy produced by an ultrasonic probe is in the form of very intense, high frequency sound vibrations, results in fragmentation of tissue (plaque and thrombosis) either as a result of mechanical action thereon or "cavitation" thereof, in which high energy ultrasound frequency applied to liquids generates vapor-filled microbubbles or "cavities" with the concomitant rapid expansion and collapse of the cavities that is accompanied by intense localized hydraulic shock, that causes fragmentation or dissolution of the tissue. Medical applications for ultrasonic probes providing cavitation include surgical procedures for ablation of tissues, for example, treatment of cancer, tissue remodeling, liposuction, and removal of vascular occlusions. Typically, ultrasonic probes described in the art for use in surgical procedures include a mechanism for irrigating an area where the ultrasonic treatment is being performed (e.g., a body cavity or lumen) to wash tissue debris from the area, and may further include an aspiration means to remove irrigation fluid and tissue debris from the site of the procedure. Mechanisms used for irrigation or aspiration described in the art are generally structured such that they increase the overall cross-sectional profile of the probe, by including inner and outer concentric lumens proximal to or within the probe to provide irrigation and aspiration channels. In addition to making the probe more invasive, prior art probes may also maintain a strict orientation of the aspiration and the irrigation mechanism, such that the inner and outer lumens for irrigation and aspiration remain in a fixed position relative to one another, which is generally closely adjacent the area of treatment. Thus, the irrigation lumen would not extend beyond the suction lumen (i.e., there is no movement of the lumens relative to one another) and any aspiration would be limited to picking up fluid and/or tissue remnants within the defined distance between the two lumens.

Ultrasonic probes described in the art for tissue ablation suffer from a number of limitations. Such probes depend on longitudinal vibration of the ultrasonic member comprising the probe i.e. vibration of the probe in the direction of the longitudinal probe axis to effect tissue fragmentation. Probe action in this modality therefore depends primarily on mechanical and thermal action of the probe tip for disrupting tissue, since the cavitational energy emanating from the tip, especially in narrow diameter probes such as those used to remove vascular occlusions, is minimal due to the small surface area of the tip itself. This primary mode of action imposes the following limitations on probe efficiency:

i) tissue ablation is restricted to very small area defined by the surface area of the probe tip, thereby necessitating time consuming surgical procedures to remove relatively large occluded areas with blood vessels in comparison to instruments which excise tissue by mechanical cutting, electrocautery, or cryoexcision methods.

ii) occurrence of late restenosis (typically within three months), and to a lesser extent acute re-occlusion after coronary angioplasty are major clinical problems limiting the long-term efficacy of ultrasonic surgical procedures for treatment of atherosclerosis and coronary angioplasty. While the pathogenosis of restenosis is still unclear, it has been demonstrated from autopsy specimens from patients with restenosis the pathophysiologic process leading to acute occlusion after coronary angioplasty is related either to a thrombotic mechanism or to major plaque dissection and superimposed thrombosis, and that these events leading to chronic restenosis involves vascular injury, platelet deposition and thrombosis and connective tissue synthesis. Such post operative processes are typically result from localized trauma at the surgical site caused by mechanical and thermal action of longitudinally vibrating probes.

Attempts to reduce some of the aforementioned problems associated with longitudinally vibrating probes have been disclosed in the art, wherein the primary action of the probe through longitudinal vibration is supplemented by a limited, supplementary transverse vibration of the probe tip i.e. perpendicular to the longitudinal axis of the probe. It is proposed that such secondary transverse vibrations in these probes will result in increased efficiency for surgical procedures. For example, U.S. Pat. No. 4,961,424 to Kubota, et al. discloses an ultrasonic treatment device that produces both a longitudinal and transverse motion at the tip of the probe. The Kubota, et al. device, however, still relies solely on the tip of the probe to act as a working surface. Thus, while destruction of tissue in proximity to the tip of the probe is more efficient, tissue destruction is still predominantly limited to the area in the immediate vicinity at the tip of the probe. U.S. Pat. No. 4,504,264 to Kelman discloses an ultrasonic treatment device, which improves the speed of ultrasonic tissue removal by oscillating the tip of the probe in addition to relying on longitudinal vibrations. Although tissue destruction at the tip of the device is more efficient, the tissue destroying effect of the probe is still limited to the tip of the probe. Both probes described in Kubota, et al., and Kelman, et al., are further limited in that the energy produced at the tip of the probe is unfocused, the action of the probe tends to push the tissue debris ahead of the probe tip. Likewise, the concentration of energy solely at the probe tip results in heating of the probe tip, which can create tissue necrosis, thereby complicating the surgical procedure and potentially compromising the recovery of the patient. Furthermore, such probes do not eliminate the problems associated with longitudinally vibrating probes.

The aforementioned limitations associated with longitudinally vibrating probes can be overcome entirely by utilizing an ultrasonic probe that vibrates exclusively in the transverse mode. Such probes are capable of generating substantially higher cavitational energy through a plurality of anti-nodes along the entire longitudinal axis of the vibrating probe, thereby eliminating the need for mechanical and thermal action at the probe tip. The advancing probe tip can therefore be shielded to prevent mechanical injury to the walls of the blood vessel for example, thereby precluding scarring, platelet deposition and clotting that lead to restenosis. Additionally, such probes are capable of tissue fragmentation over greater surface area (along the entire longitudinal axis) resulting in high efficiency, thus allowing for rapid surgical procedures and substantially eliminating thermal effects on tissue caused by prolonged probe operation.

Since probe vibrating exclusively in a transverse mode is entirely dependent on cavitational energy for their action, important factors for maintaining efficiency of such probes are (i) narrow probe diameter to facilitate oscillation at lower ultrasonic energies and (ii) increased longitudinal axis (probe length) that results in more cavitation anti-nodes. Although narrow probe diameters are advantages especially for negotiation through narrow blood vessels and occluded arteries, the utilization of such probes have been precluded by inability to effectively control the vibrational amplitude of thin probes, that result in potential damage to the probe and greater risk, of tissue damage resulting from their use. The use of narrow diameter probes have been disclosed in the art for providing greater maneuverability ease of insertion in narrow blood vessels. U.S. Pat. No. 4,920,954 to Allinger discloses a narrow diameter ultrasonic device wherein a rigid sleeve is used to prevent transverse vibrations U.S. Pat. No. 5,380,274 discloses a narrow diameter probe for improved longitudinal vibration having a sheath to inhibit transverse vibration U.S. Pat. No. 5,469,853 to Law discloses a thin, longitudinally vibrating ultrasonic device with a bendable sheath that facilitates directing the probe within narrow blood vessels. While the prior art has focused on the need for using sheaths on thin ultrasonic devices, their use has been entirely to prevent transverse, vibrations of the device and to protect such devices from damage resulting from such vibrations Based on the aforementioned limitations of ultrasonic probes in the art, there is a need for ultrasonic probe functioning in a transverse mode that further obviates the shortcomings of that further overcomes limitations imposed by of narrow diameter requirements for efficient operation of such probes for rapid tissue ablation. Transversely vibrating ultrasonic probes for tissue ablation are described in the Applicant's co-pending provisional applications U.S. Ser. Nos. 60/178,901 and 60/225,060, and 09/776,015 which further describe the design parameters for such a probe its use in ultrasonic devices for tissue ablation. The entirety of these applications are herein incorporated by reference.

There is a further need for controlling the for procedures which require precise delivery of cavitation energy to defined locations, to be able to restrict the cavitation energy emanating circumferentially from a transversely vibrating p at multiple anti-nodes wastes a portion of the energy given off by the probe, as the energy is unfocused and dispensed along the length of the probe.

There is also a need in the art for a means of focussing the cavitational energy emitted by such a probe to deliver the energy to exactly to the desired location within a blood vessel while shielding the surrounding tissue from damage.

SUMMARY OF THE INVENTION

The present invention is directed towards a transversely vibrating ultrasonic probe for tissue ablating surgical devices that overcomes the aforementioned limitations of ultrasonic probes in the art used for this application. Particularly, the present invention is directed towards providing a means to control, direct and focus the cavitation energy from a transversely vibrating ultrasonic probe by utilizing a sheath assembly extending circumferentially along the longitudinal axis of the probe. In accordance with the present invention, there is provided an ultrasonic probe operating in a transverse mode whereby the probe is cable of vibrating in a direction perpendicular to its longitudinal axis upon application of an ultrasonic frequency, capable of precisely focussing or directing the cavitation energy of the probe to defined regions within a blood vessel. The object of this invention can be accomplished by a transversely vibrating ultrasonic probe described in a co-application submitted by the applicants (###) the entirety of which is herein incorporated by reference.

Further in accordance with the invention, a sheath, a sleeve or other damping member provided with fenestrations is a sheath that is adapted circumferentially along the probe axis, thereby providing control over release of cavitation energy in specific regions along the probe axis. Non-fenestrated areas of the said sheath or sleeve effectively block cavitation energy emanating from the probe from such areas.

Still further in accordance with the invention, a sheath assembly comprising one or more sheaths may can be adapted to the ultrasonic probe, thereby providing a means of containing, focussing, and transmitting energy generated along the length of the probe to one or more defined locations. The sheaths of the present invention also provide the user with a means of protecting regions of tissue from physical contact with the probe. In one embodiment of the invention he sheaths also comprise a means for aspiration and irrigation of the region of probe activity, as well as a means of introducing a drug or compound to the site of probe activity.

In one aspect, a plurality of sheaths are used in combination to provide another level of precision control over the direction of cavitation energy to a tissue in the vicinity of the probe. In one embodiment of the invention, the sheath encloses a means of introducing fluid into the site of the procedure, and a means for aspirating fluid and tissue debris from the site of the procedure. In another aspect the sheath assembly further encloses a means of introducing a drug intravascularly that dissolves clots and prevents the recurrence of stenosis. The ultrasonic oscillation of the probe of the present invention will be used to facilitate the penetration of antithrombogenic agents into the vascular or luminal walls to inhibit restenosis. Preferred antithrombogenic agents include heparin, hirudin, hirulog, urokinase, streptokinase, tPA, and similar agents. In a further embodiment, the probe tip can be moved within the sheath. In yet another aspect, the irrigation and aspiration means, and the probe tip, can all be manipulated and repositioned relative to one another within the sheath. In another embodiment, the sheath is shaped in such a way that it may capture or grasp sections of tissue that can be ablated with the probe.

Still further in accordance with the invention, the sheath provides a guide for the probe tip, protecting tissues from accidental puncture by the sharp, narrow-diameter tip, or from destruction by energy emitted radially from the probe during introduction of the probe to the site. The sheath may be applied either to the probe tip prior to insertion of the probe into the patient, or pre-inserted into the patient prior to the insertion of the probe. The sheath of the present invention can be used to fix the location of one or more shapes relative to the nodes or anti-nodes of a probe acting in transverse action. The location of the reflective shapes can amplify the acoustical wave thereby magnifying the energy. This allows for the use of very small diameter probes which themselves would not have the requisite structural integrity to apply and translate acoustical energy into sufficient mechanical energy to enable ablation of tissues. The reflective shapes can also focus or redirect the energy, effectively converting a transverse probe emitting cavitation energy along its length, to a directed, side fire ultrasonic device.

In a still further aspect of the invention the probe emits transverse ultrasonic energy along its longitudinal axis that may be used to, for example, fragment abnormal cells on the surface of the body cavity which come within the sweep of the probe, or to clear obstructions and constrictions within vasculature or tissue lumen. The device is designed to have a small cross-sectional profile, which also allows the probe to flex along its length, thereby allowing it to be used in a minimally invasive manner. In one aspect, the probe be at least partially contained within the sheath to contain, focus, intensify, and direct the emitted cavitation energy to specific target tissue sites. In another embodiment of the invention, a plurality of sheaths are used in combination to provide another level of precision control over the direction of cavitation energy to a tissue in the vicinity of the probe.

Still further in accordance with the invention, the sheath encloses a means of introducing fluid into the site of the procedure, and a means for aspirating fluid and tissue debris from the site of the procedure. In a further embodiment, the probe tip can be moved within the sheath. In one aspect, the irrigation and aspiration means, and the probe tip, can all be manipulated and repositioned relative to one another within the sheath. In another aspect, the sheath is shaped in such a way that it may capture or grasp sections of tissue that may be ablated with the probe. In yet another embodiment, the sheath provides a guide for the probe tip, protecting tissues from accidental puncture by the sharp, narrow diameter tip, or from destruction by energy emitted radially from the probe. The sheath may be applied to the probe tip prior to insertion of the probe into the patient, or the sheath can be inserted into the patient prior to the insertion of the probe.

The sheath of the present invention can be used to fix the location of one or more shapes relative to the energy nodes or anti-nodes emitted by a transversely vibrating probe. The location of and the particular shape can modulate the energy emitted from the probe at one site, and communicate it to a distant site, for example, it may amplify the acoustical wave at one or more energetic anti-nodes, thereby increasing the energy emitted at the sheath's aperture. This allows for the use of very small diameter probes which themselves would not have the requisite structural integrity to apply and translate acoustical energy into sufficient mechanical energy to enable ablation of tissues. The reflective shapes can also focus or redirect the energy, effectively converting a transverse probe emitting cavitation energy along its length, to for example, a directed, "side-fire" ultrasonic device.

BRIEF DESCRIPTION OF THE DRAWINGS

In the drawings, like reference characters generally refer to the same parts throughout the different views. The drawings shown are not necessarily to scale, with emphasis instead generally being placed upon illustrating the principles of the invention.

FIG. 4 shows a probe that is substantially contained within a sheath comprising a plurality of fenestrations.

FIG. 5 shows a probe that is substantially contained within a sheath assembly comprising a plurality of adjustable sheaths.

DETAILED DESCRIPTION OF INVENTION

Figure 1:
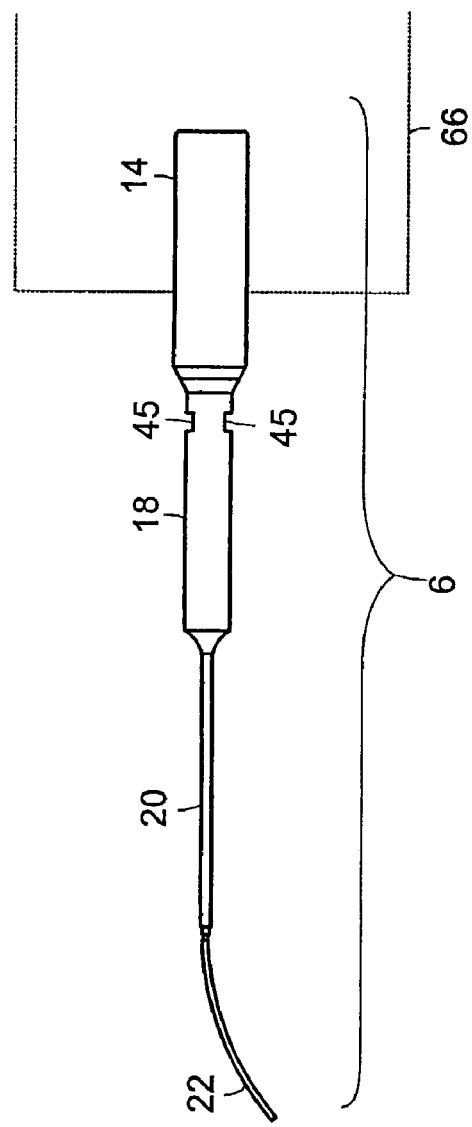
FIG. 1 illustrates an exemplary ultrasonic device comprising the ultrasonic probe tip constructed in accordance with the principles of the present invention

The following terms and definitions are used herein:

"Anti-node" as used herein refers to a region of maximum energy emitted by an ultrasonic probe on or proximal to a position along the probe.

"Cavitation" as used herein refers to shock waves produced by ultrasonic vibration, wherein the vibration creates a plurality of microscopic bubbles which rapidly collapse, resulting in molecular collision by water molecules which collide with force, thereby producing the shock waves.

"Cross-sectional diameter" as used herein refers to the diameter of the cylindrical regions of the probe, including the probe tip.

"Fenestration" as used herein refers to an aperture, window, opening, hole, or space.

"Node" as used herein refers to a region of minimum energy emitted by an ultrasonic probe on or proximal to a position along the probe.

"Probe" as used herein refers to a device capable of being adapted to an ultrasonic generator means, which is capable of propagating the energy emitted by the ultrasonic generator means along its length, and is capable of acoustic impedance causing transformation of ultrasonic energy into mechanical energy.

"Sheath" as used herein refers to an apparatus for covering, encasing, or shielding in whole or in part, a probe or portion thereof connected to an ultrasonic generation means.

"Transverse" as used herein refers to vibration of a probe at right angles to the axis of a probe. A "transverse wave" as used herein is a wave propagated along an ultrasonic probe in which the direction of the disturbance at each point of the medium is perpendicular to the wave vector.

"Tuning" as used herein refers to a process of adjusting the frequency of the ultrasonic generator means to select a frequency that establishes a standing wave along the length of the probe.

The present invention provides an ultrasonic medical device for tissue ablation. More particularly the present invention provides an ultrasonic device comprising a probe capable of vibrating ultrasonically in a transverse mode causing generation of cavitational energy circumferentially around the said probe, comprising a protective sheath assembly adapted over the probe that is capable of focussing, directing and modulating the cavitational energy emitted by the probe. The sheath assembly of the invention allows the user to optimize the tissue ablation efficiency of the probe to suit a particular medical procedure.

The probe of the invention is capable of removing tissue at sites wherein the probe makes actual contact with the tissue, and typically in a region that is radially disposed (approximately 2 mm) from the probe, that corresponds to the region of maximum cavitational energy or "anti-nodes" emanating perpendicular to the longitudinal axis of the probe. By eliminating the axial motion of the probe and allowing transverse vibrations only, fragmentation of large areas of tissue spanning the entire length of the probe due to generation of multiple cavitational anti-nodes along the probe length perpendicular to the probe axis. Since substantially larger affected areas within an occluded blood vessel can be denuded of the occluded tissue in a short time, actual treatment time using the transverse mode ultrasonic medical device according to the invention is greatly reduced as compared to methods using pilot art probes that primarily utilize longitudinal vibration (along probe axis) for tissue ablation. Because the thinnest region of the probe is capable of providing, multiple energy anti-nodes along its length, it is desirable to have a means of modulating this energy, thereby providing a precise way of delivering the energy selectively to desired locations, such as for example an occluded region within a blood vessel, while protecting nearby tissues both from the fragmenting energy and physical damage (for example, punctures) from the narrow diameter probe tip. The probe equipped with a sheath assembly such as that described herein, provides a means for modulating the intensity and direction of energy emitted from such a probe. Additionally, the probe equipped with the sheath assembly of the invention provides a more efficient, selective means of delivering energy from the probe to a specific tissue space, or tissue space, for example at the site of an occlusion within a blood vessel, causing rapid fragmentation and ablation of said tissue without detrimental effect other areas within the vessel.

Probes of the present invention are described in the Applicant's co-pending provisional applications U.S. Ser. Nos. 60/178,901 and 60/225,060 which further describe the design parameters for an ultrasonic probe operating in a transverse mode and the use of such a probe to remodel tissues. The entirety of these applications are herein incorporated by reference.

The present invention allows the selective application of cavitation energy emitted from an ultrasonic probe to tissue. The probe is adapted to an ultrasonic generator means that selectably provides energy over a frequency range of from about 20 kHz to about 80 kHz. In the currently preferred embodiment, the frequency of ultrasonic energy is from 20,000 Hertz to 35,000 Hertz. Frequencies in this range are specifically destructive of hydrated (water-laden) tissues, while substantially ineffective toward high-collagen connective tissue, or other fibrous tissues such as skin or muscle tissues. The amount of cavitation energy to be applied to a particular site requiring treatment is a function of the amplitude and frequency of vibration of the probe, as well as the longitudinal length of the probe tip, the proximity of the tip to a tissue, and the degree to which the probe tip is exposed to the tissues. Control over this last variable can be effectuated through the sheath of the present invention.

A significant advantage of the ultrasonic medical device of the invention is that it physically destroys and removes undesired tissue through the mechanism of cavitation, which is non-thermal. As a consequence, the complications which are arise from thermal destruction or necrosis of tissue are not observed. The increase in local temperature is most likely a result of the heating of the probe. By using the probe contained within a sheath of the present invention the probe is substantially contained and isolated from direct contact with the tissues, thereby enabling destruction of tissues with only a small increase in local temperature, about 7° C. from normal body temperature. The use of a sheath further diminishes or prevents the local temperature rise. Accordingly, In one embodiment, the sheath of the present invention provides a means of insulating surrounding tissue from the thermal side effects of the ultrasonic probe.

The length and diameter of the sheath used in a particular surgical procedure is dependent on the type of probe used, the degree to which the probe length will be inserted into the patient, and the degree of shielding that is required based on the specific areas to be treated. For example, in an application whereby prostate tissue is removed via an intra-urethral route with the ultrasonic probe of the present invention, the sheath must be of a sufficient length to protect the tissue of the urethra, of a sufficient outside diameter to facilitate insertion of the sheath into the urethra, and a sufficient inside diameter capable of accepting the probe. By contrast, for tissue remodeling near, for example, the eye, a probe useful for such a procedure would be significantly shorter and of a significantly smaller diameter, and as such, so would the sheath. The exact dimensions of the sheath including its length and diameter is determined by requirements of a specific medical procedure. Similarly, as illustrated in FIGS. 3 and 4, the position and size of the sheath aperture 111, or number and positions of the fenestrations 111, or the presence of a bevel on the sheath terminus 129 to provide a means for tissue manipulations, will likewise be determined by the type of procedure, and the requirements of the particular patient.

In one aspect of the invention, as shown in FIG. 5, the sheath comprises an inner sheath 121 and an outer sheath 108. The outer sheath may be connected to a retraction trigger (not shown), by one or more articulation means, such as wires, which is capable of moving the outer sheath with respect to the inner sheath. Each wire comprises a first end and a second end. The first end is affixed to the outer sheath 108, while the second end is affixed to a retraction trigger. When the outer sheath 108 is slid back away from the terminus of the inner sheath 121 the tissues are exposed to cavitation energy emitted by the probe.

In another embodiment, the sheath is flexible. Articulation wires (not shown) comprising two ends, are connected to the sheath and an articulation handle. When the articulation handle is manipulated, for example, pulled axially inward, the flexible sheath will bend or articulate in a bending or articulation direction A, thereby causing the ultrasonic probe to bend or articulate in articulation direction A. In this way, the ultrasonic probe can be used to reach locations that are not axially aligned with the lumen or vessel through which the sheath and probe are inserted.

Figure 6:
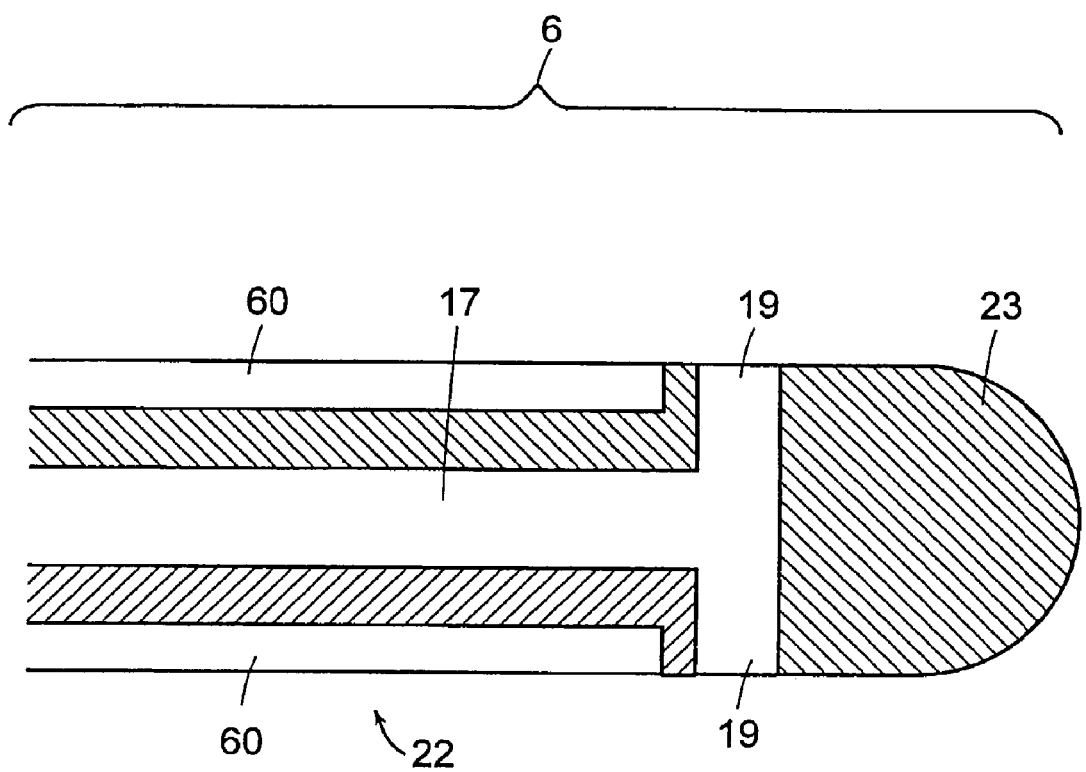
FIG. 6 shows a longitudinal cross-sectional view of the distal end of the probe comprising a central irrigation passage, lateral irrigation lumens and external aspiration channels.
Figure 7:
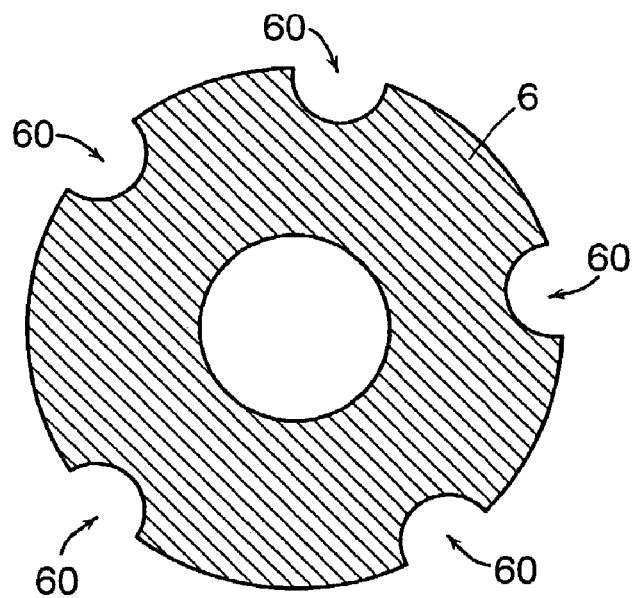
FIG. 7 shows a transverse cross-sectional view of a portion of the probe illustrating the irrigation and aspiration channels.

A particular advantage of the ultrasonic probe operating in transverse mode is that the efficient cavitation energy produced by the probe disintegrates target tissue to small particles of approximately 5 microns in diameter. Because of the operation of the probe, tissue debris created at the probe tip is propelled in a retrograde direction from the probe tip. Accordingly, in another embodiment of the invention, the sheath provides at least one aspiration channel, which can be adapted to a vacuum or suction device, to remove the tissue debris created by the action of the probe. The aspiration channel can be manufactured out of the same material as the sheath provided it is of a sufficient rigidity to maintain its structural integrity under the negative pressure produced by the aspiration means, for example a vacuum pump or other source of negative pressure. Such an aspiration channel is provided either inside the lumen of the sheath, or along the exterior surface of the sheath, or both. In these embodiments, the aspiration channel can be a second hollow sheath nested within the first sheath, or the aspiration channel can be formed in the body of the sheath. A preferred embodiment is shown in FIGS. 6 and 7, whereby the probe 22 itself has one or more grooves defining one or more aspiration channels 60, and aspiration of tissue debris is effectuated along the probe length between the interior surface of the sheath and the exterior surface of the probe, as directed by the aspiration channels and by retrograde flow from the probe action. FIG. 6 shows a longitudinal cross-section of a portion of an ultrasonic probe 22 and tip 23 according to one embodiment of the invention, comprising a central irrigation passage 17 and lateral irrigation lumens 19, as well as external aspiration channels 60. The sheath, not shown, would surround the probe.

In another embodiment, the sheath of the present invention comprises an irrigation channel. The sheath is adapted to an irrigation means, for example, a peristaltic pump or other such device for delivering liquids under controlled flow rates and pressures, and the sheath directs fluid to the location of the probe. The irrigation channel can be manufactured out of the same material as the sheath provided it is of a sufficient rigidity to maintain its structural integrity under the positive pressure produced by the flow of fluid produced by the irrigation means. Such an irrigation channel is provided either inside the lumen of the sheath, or along the exterior surface of the sheath, or both. In these embodiments, the irrigation channel can be a second hollow sheath nested within the first sheath, or the irrigation channel can be formed in the body of the sheath. In one embodiment, the probe itself has one or more grooves defining irrigation channels, and fluid is directed along the probe length between the interior surface of the sheath and the exterior surface of the probe, as directed by the irrigation channels. In this embodiment, irrigation fluids provide a means of cooling the probe. The sheath itself, or an irrigation sheath contained within the first sheath can provide a means of introducing a drug or pharmaceutical formulation to the site of probe activity. For example, anti-thrombolytic drugs such as heparin, streptokinase, tPA, urokinase, hirulog, or hirudin may be introduced to the site of a vascular occlusion through the sheath. The ultrasonic energy further provides a means for assisting the drug in penetrating the occlusion.

In yet another embodiment, the sheath of the present invention further comprises both an irrigation and an aspiration channel. As in the above embodiments, the channels may be located within the sheath lumen, or exterior to the sheath, or a combination of the two, and can be proximal or distal to the other channel provided they are not in direct communication. Likewise, in these embodiments the probe itself has a plurality of grooves defining aspiration channels and irrigation channels, and fluid is directed along the probe length between the interior surfaces of the sheaths and the exterior surface of the probe, as directed by the aspiration and irrigation channels. In another aspect of the invention, the sheath comprises a means for directing, controlling, regulating, and focussing the cavitation energy emitted by the probe, an aspiration means, an irrigation means, or any combination of the above.

Figure 8:
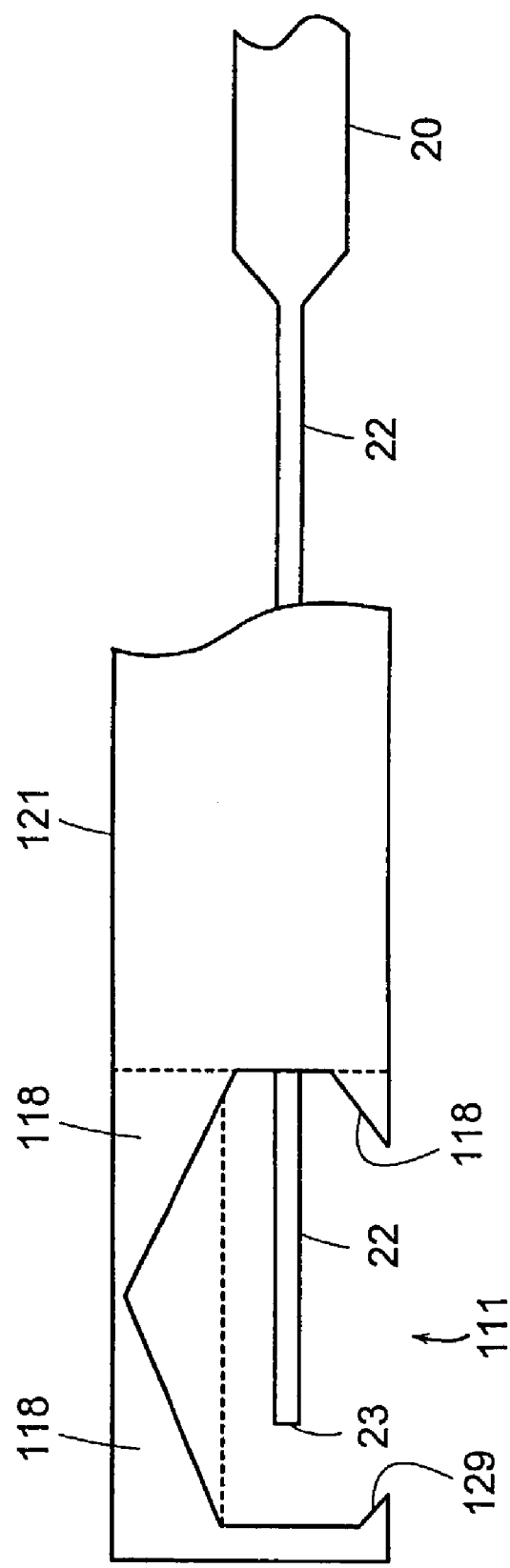
FIG. 8 are longitudinal cross-sectional views of the distal end of the probe contained within sheaths incorporating angled reflective elements.

In yet another embodiment, as shown in FIG. 8, the sheath is a device that allows for the manipulation of tissues, comprising a surface that is capable of manipulating tissues near the site of the probe. In this aspect, the terminus of the sheath may be closed, such that the sheath insulates tissues from the destructive energy emitted by the probe and can be used to push tissues away from the aperture 111, thereby allowing proximal tissues to be exposed to the probe 22 and 23. Alternatively, the sheath comprises a beveled or arcuate surface at the sheath terminus 129, capable of providing a means for hooking, grasping, or otherwise holding a tissue in proximity to the probe 22 and 23. In another embodiment, the sheath allows for the introduction of another surgical device, for example, flexible biopsy forceps, capable of manipulating tissues into a tissue space, such that the surgical device can hold the tissue in proximity with the probe.

In a further embodiment, the internal surface of the sheath provides a means to amplify or focus cavitation energy from the probe 22. In this aspect, the interior surface of the sheath comprises at least one structure or reflective element 118, that extends into the sheath lumen. The reflective element maybe planar, or arcutate, or a combination of these shapes. Reflective elements of the present invention may be fabricated from the same material as the sheath, or may use different materials that optimize the reflective properties of the elements. Since the cavitation energy reaches a maximum at anti-nodes along the probe, the interval of the anti-nodes being determined by the ultrasonic frequency at which the generator operates, the spacing of the reflective elements in the sheath is determined by the intended operating frequency of the ultrasonic device. Similarly, the number of anti-nodes along the probe 22, is determined by the length of the probe and the frequency. As such, the number of reflective elements is determined by the length of the probe and the operating frequency. For example, an ultrasonic device operating at a frequency of approximately 25 kHz employing a probe with a length at the thinnest interval 22 of about 3 centimeters, will display about seven anti-nodes approximately 2 millimeters wide, spaced about 2 millimeters apart. Energy will radiate circumferentially around the probe at these anti-nodes. A sheath useful with such a probe would comprise, for example but not limited to, a cylindrical sheath about at least 3 centimeters in length further comprising seven reflective elements, approximately 2 millimeters wide, spaced about 2 millimeters apart, positioned with respect to the probe such that the reflective elements 118, are centered over the anti-nodes. Since the energy emitted by the probe radiates circumferentially from an antinode, the reflective elements can extend radially from the interior wall of the sheath into the sheath lumen, for example, 270 degrees around the interior of the sheath, while the remaining 90 degrees has no reflective element and thereby provides a means for channeling the cavitation energy from the anti-node to a position distal to the anti-node. The channeling means of the present example maybe a region where no reflective element is present, or where the shape or angle is altered compared to the reflective element, or any other such means of directing energy from the area of the anti-node to a position distal to the anti-node.

The sheath of the present invention may comprise a means of viewing the site of probe action. This may include an illumination means and a viewing means. In one embodiment, the sheath of the present invention comprises a means for containing or introducing (if external to the sheath) an endoscope, or similar optical imaging means. In another embodiment of the invention, the ultrasound medical device is used in conjunction with an imaging system, for example, MRI, or ultrasound imaging—in particular color ultrasound. In this embodiment, the action of the probe echogenically produces a pronounced and bright image on the display. The sheath in this embodiment shields the probe, thereby reducing the intensity of the probe image and enhancing the resolution of the image by decreasing the contrast between the vibrating probe and the surrounding tissues.

In yet another embodiment, the sheath assembly of the present on may be provided along with an ultrasonic probe in the form of a kit. In this aspect, the probe for a particular surgical procedure is provided, along with the correct sheath, as well as instructions for assembling and tuning the probe, and the appropriate frequency range for the procedure. The probe and sheath may be packaged preassembled, such that the probe is already contained within the sheath and the respective position of the probe within the sheath is optimized such that any reflective elements in the sheath would be correctly aligned with the prospective position of the anti-nodes for a given frequency, the kit further comprising instructions for the appropriate frequency. The kit may further comprise packaging whereby the probe and sheath are pre-sterilized, and sealed against contaminants. In a preferred embodiment, the probe and sheath are provided in a container that complies with regulations governing the storage, handling, and disposal of sharp medical devices. Such a container is capable of receiving and securing the probe and sheath before and after use. In one aspect, the sharps container provides a means of affixing the probe and sheath assembly to an ultrasonic medical device without direct manipulation of the probe and sheath assembly, and a means for removing the assembly from the ultrasonic medical device after use. In another aspect, the kit comprises a probe and sheath assembly contained within a sterile sharps container that further comprises a single use locking means, whereby the probe and sheath assembly is affixed to the ultrasonic medical device solely through the sharps container, are removed from device solely through the container, and once removed can not be re-extracted from the sharps container.

Referring now to FIG. 1, a transverse mode ultrasonic medical device comprising an elongated probe 6 which is coupled to a device providing a source or generation means for the production of ultrasonic energy (shown in phantom in the Figure as 66) constructed in accordance with the present invention is illustrated. The generation source may or may not be a physical part of the device itself. The probe 6 transmits ultrasonic energy received from the generator along its length. The probe is capable of engaging the ultrasonic generator at one terminus with sufficient restraint to form an acoustical mass that can propagate the ultrasonic energy provided by the generator. The other terminus of the probe comprises a tip 22, which has a small diameter, enabling the tip to flex along its longitude. In one embodiment of the invention, the probe diameter decreases at defined regional or segment intervals 14, 18, 20, and 22. Energy from the generator is transmitted along the length of the probe, causing the probe segments 22 and 23 at the distal end to vibrate in a direction that is transverse to the probe longitudinal axis. In this embodiment, one of the probe intervals 18 has at least one groove 45 for engaging the locking assembly of a probe disposal container.

Figure 2:
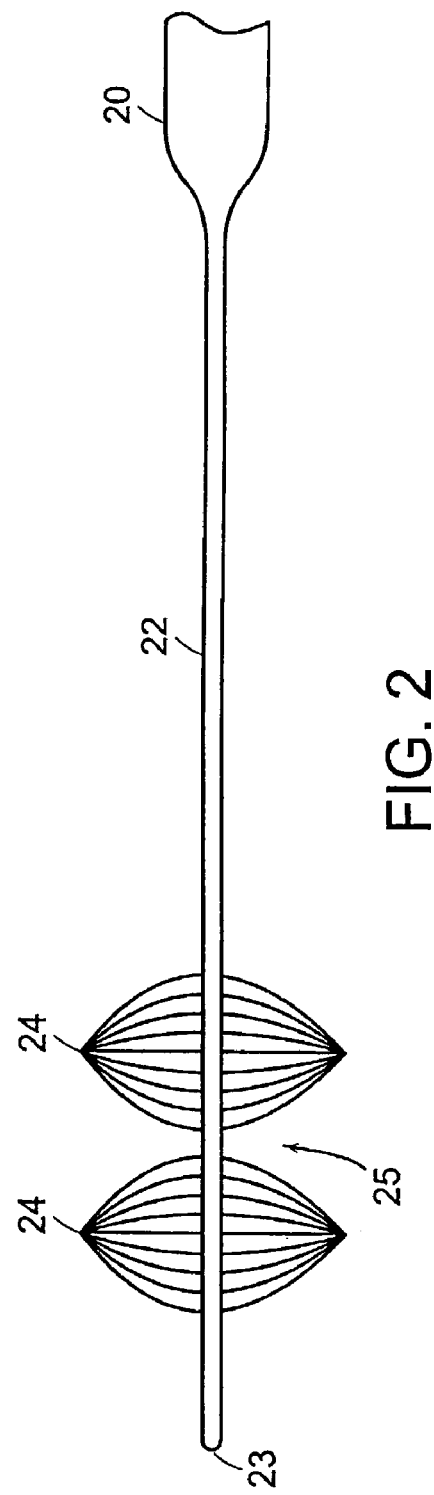
FIG. 2 shows the areas of maximum vibrations (anti-nodes) and minimum vibrations (nodes) caused by transverse, vibration of probe and probe tip.

Referring now to FIG. 2, the terminal segment 22 and tip 23 of the probe are illustrated, wherein transverse vibration caused by application of ultrasonic energy to the probe generates alternating areas of maximum vibration, or "anti-nodes" 24, along the length of the probe segment 22 and tip 23, and "nodes," or areas of minimum vibration 25, at repeating intervals along said segment and tip. The number of anti-nodes, and their spacing along the probe depends on the frequency of the energy produced by the ultrasonic generator, while the separation of nodes and anti-nodes is a function of harmonic intervals of the frequency, and can be affected by tuning the probe. In a properly tuned probe, the anti-nodes will be found at a position exactly one half of the distance between the nodes. Tissue-destroying effects of the device are not limited to regions coming into direct contact with probe tip 23, but rather, as the probe is moved through the area where ablation is desired, tissue is removed in areas adjacent to the multiplicity of anti-nodes produced along the entire length of the probe. The magnitude of the cavitation energy produced by the probe tip is such that it extends outward from the probe tip at the anti-nodes from about 1-2 millimeters.

Figure 3A:
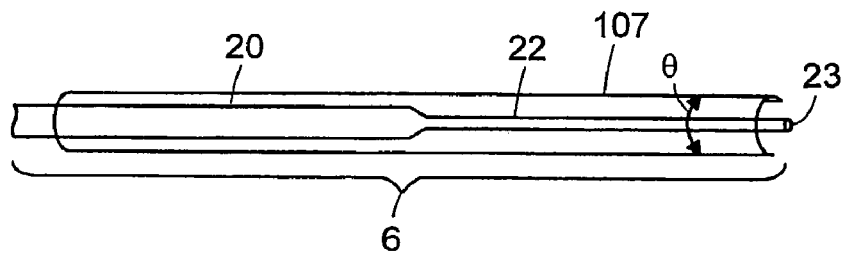
FIGS. 3a-g show different configurations of sheaths comprising the sheath assembly adapted to the probe.
Figure 3B:
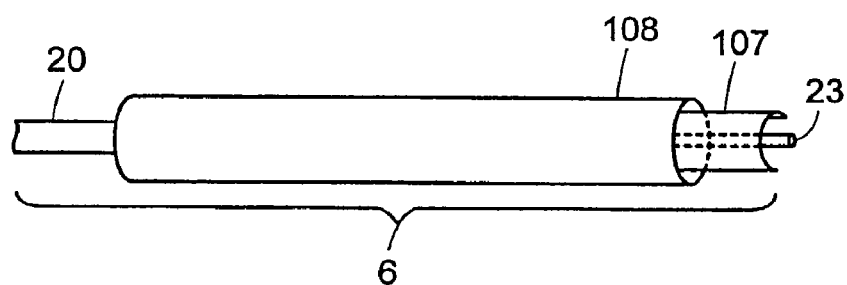
Figure 3C:
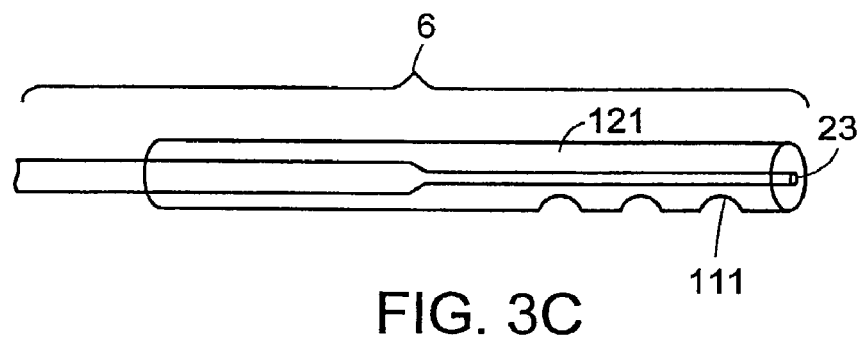
Figure 3D:
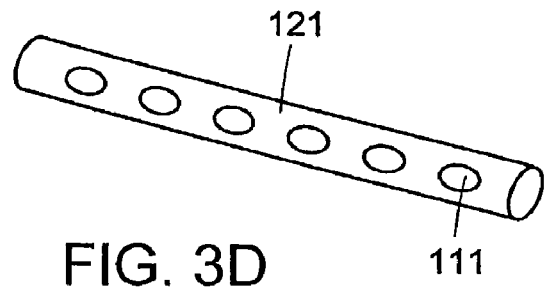
Figure 3E:
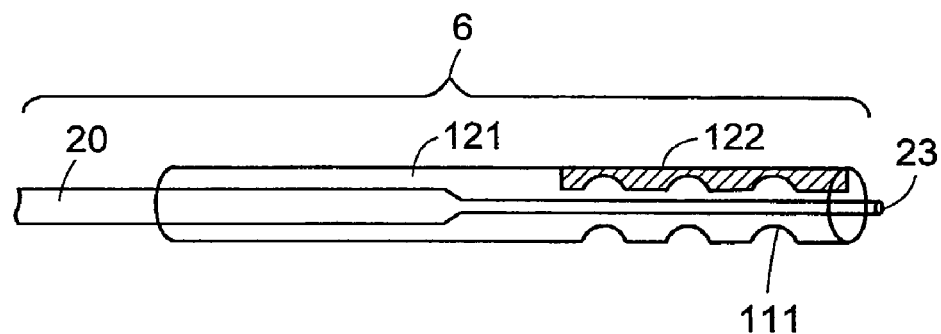
Figure 3F:
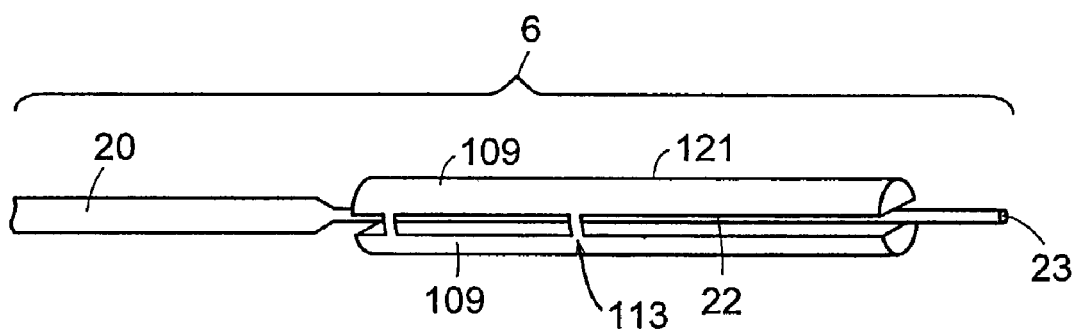
Figure 3G:
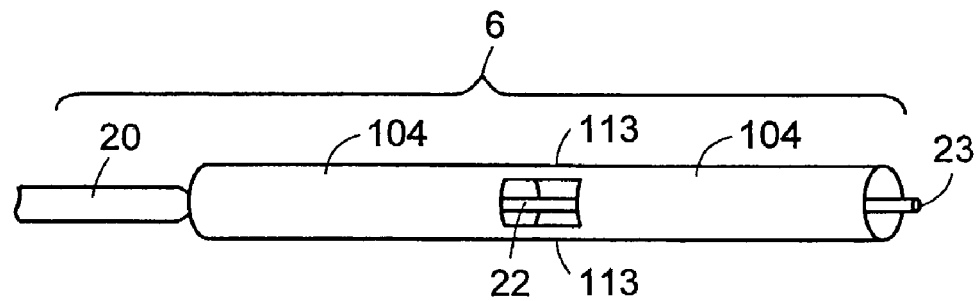

Referring now to FIGS. 3a-g, sheath assemblies comprising different configurations of dampening sheaths for the ultrasonic probe 6 are illustrated. FIG. 3a shows a transverse mode probe 6 is shown comprising a semi-cylindrical sheath 107, which partially contains the probe. For purposes of illustration, the probe 6 is visible beneath the sheath. The sheath 107 is of a sufficient diameter, so as to at least partially encompass the probe. In the semi-cylindrical embodiment shown, the circumference of the sheath is approximately 180 degrees, and the length is sufficient to span a plurality of intervals 20 and 22 over the probe. FIG. 3b shows a semi-cylindrical sheath 107 (also shown in FIG. 2), and a second concentric sheath 108 that is cylindrical, and is capable of containing the first sheath 107, as well as the probe 6. FIG. 3c shows the sheath 121 having a cylindrical structure of a sufficient diameter to contain the probe 6, made visible for the purpose of illustration. Sheath 121 comprises at least one fenestration 111, which allows the cavitation energy emitted from the probe tip to be communicated to an area outside the sheath, through the said fenestration; probe energy from areas wherein the probe is not exposed by a fenestration is contained by the sheath. FIG. 3d shows the hollow cylindrical sheath 121 containing a plurality of arcutate fenestrations 111. FIG. 3e illustrates a longitudinal view of probe 6 contained within a sheath 121 which comprises a plurality of arcutate fenestrations 111, and at least one acoustic reflective element 122, that is adapted to the interior surface of the sheath. FIG. 3f shows a sheath 121 further comprising two semi-cylindrical halves 109, each half connected to the other by one or more connecting means 113. The probe 6 is capable of being substantially contained within the sheath. The cavitation energy generated by the probe tip 22 is contained by the semi-cylindrical halves 109, where they occlude the probe tip. FIG. 3g illustrates a sheath further comprising of at least two cylinders 104, each cylinder connected to the other by at least one connecting means 113. The probe 6 is capable of being substantially contained within the sheath. The cavitation energy generated by the probe tip 22 is contained by cylinders 104, where they occlude the probe tip.

Referring now to FIG. 4, a segment 20 of a probe is substantially contained in a sheath 121 comprising a plurality of fenestrations 111. Release of cavitation energy emitted by the probe 20, to the environment is controlled by sheath 121 and is communicated to the outside of the sheath through the fenestrations.

Referring now to FIG. 5, the distal end of the probe of ultrasonic medical device contained in a sheath assembly is illustrated. The probe 6 is substantially contained within a cylindrical sheath 121 capable of modulating the energy omitted by an active probe, and shielding tissues from puncture from a sharp probe tip. The sheath 121 shown in this illustration has been modified such that one of the terminal ends of the sheath is substantially open, defining a fenestration or aperture 111, which exposes the probe tip 22 and 23. The terminus of the sheath 129 is shaped to provide a means for manipulating tissue to bring it into proximity with the probe 22 and 23. A second concentric cylindrical sheath 108 which surrounds a portion of the first sheath 121, that can be manipulated longitudinally along the first sheath to provide a means for modulating the exposure of the probe tip 22 and 23 by partial closure of the aperture 111, thereby modulating the cavitation energy emitted by the probe to which occlusion materials will be exposed.

Referring now to FIG. 6, a longitudinal cross-section of a portion of an ultrasonic probe tip 22 and 23 is shown, comprising a central irrigation passage 17, lateral irrigation lumens 19, and as external aspiration channels 60.

Referring now to FIG. 7, a transverse cross-sectional view of a portion of the ultrasonic probe shown. The probe 6 comprises a plurality of arcutate channels 60 that extend over the longitudinal length of the probe tip, providing a conduit for irrigation and or aspiration of tissue debris and fluid.

Referring now to FIG. 8, sheath comprising a fenestration 111 allowing communication of the cavitation energy emitted by the probe to the outside of the sheath is shown. The interior of the sheath further comprises reflective elements 118, shown as a plurality planar surfaces that extend from the interior wall of the sheath into the lumen, thereby providing a means for focusing and redirecting cavitation energy emitted by the probe tip. In embodiment, the terminus of the sheath 129 is shaped to provide a tissue manipulation means.

Figure 9:
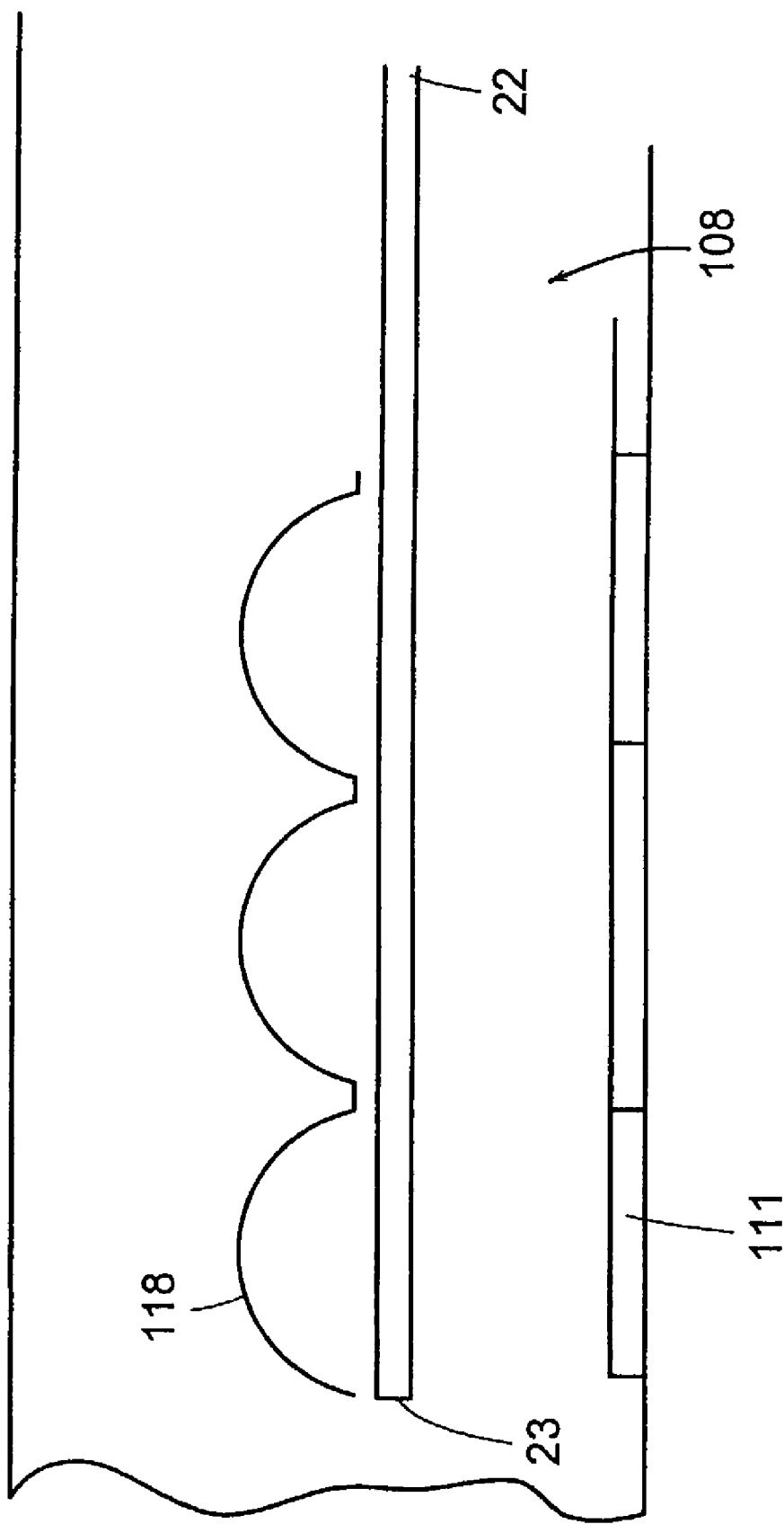
FIG. 9 are longitudinal cross-sectional views of the distal end of the probe contained within sheaths incorporating arctuate of reflective elements

Referring now to FIG. 9, a sheath comprising a fenestration 111 allowing communication of the cavitation energy emitted by the probe to the outside of the sheath is shown. The interior of sheath 121 containing the probe 22 and 23 comprises reflective elements 118 that are arcuate, and contain a plurality of fenestrations 111.

Sheath materials useful for the present invention include any material with acoustical or vibrational dampening properties capable of absorbing, containing, or dissipating the cavitation energy emitted by the probe tip. Such materials must be capable of being sterilized by, for example, gamma irradiation or ethylene oxide gas (ETO), without losing their structural integrity. Such materials include but are not limited to, plastics such as polytetrafluoroethylene (PTFE), polyethylene, polypropylene, silicone, polyetherimide, or other such plastics that are used in medical procedures. Ceramic materials can also be used, and have the added benefit that they may be sterilized by autoclaving. Combinations of the aforementioned materials can be used depending on the procedure, for example as in the sheath of FIG. 5, a ceramic sheath 121 can be used in combination with a moveable PTFE outer sheath 108. Alternatively a single sheath may employ two or more materials to give the desired combination of strength and flexibility, for example, the sheath may comprise a rigid ceramic section distal to the probe tip 23 and a more flexible plastic section proximal to the tip, capable of flexing with the probe 22. In the currently preferred embodiment of the invention, PTFE is used to fabricate a strong, flexible, disposable sheath that is easily sterilized by irradiation or ETO gas.

It should be obvious to those of ordinary skill in the art that the individual features described herein may be combined. Variations, modifications, and other implementations of what is described herein will occur to those of ordinary skill in the art without departing from the spirit and scope of the invention as claimed. Accordingly, the invention is to be defined not by the preceding illustrative description but instead by the spirit and scope of the following claims.

We claim:

1. An ultrasonic medical device for tissue ablation comprising:
    an elongated probe having a proximal end, a distal end and at least two regions of differing cross sectional dimension, wherein a length of the elongated probe is configured to oscillate in a direction transverse to a longitudinal axis of the elongated probe to emit transverse ultrasonic energy along the length of the elongated probe so that a plurality of transverse nodes and transverse anti-nodes are formed along the length of the elongated probe; and
    a sheath assembly at least partially surrounding the elongated probe, the sheath assembly comprising at least one sheath defining a fenestration between a proximal and distal end of the at least one sheath, the at least one sheath being configured to substantially dampen ultrasonic energy such that ultrasonic energy delivered by the elongated probe is focused toward a region adjacent the fenestration.

2. The device of claim 1, wherein the sheath assembly covers at least a portion of the elongated probe, the sheath assembly comprising a longitudinally extending structural wall that defines a longitudinally extending hollow interior for accommodating at least a portion of the elongated probe, wherein the longitudinally extending structural wall of the sheath assembly is substantially self supporting so that the longitudinally extending structural wall substantially maintains a same shape with the elongated probe disposed in the longitudinally extending hollow interior as without the elongated probe disposed in the longitudinally extending hollow interior.

3. The device of claim 1, wherein the sheath assembly is constructed to substantially prevent a transmission of cavitational energy generated by the elongated probe to a surrounding environment.

4. The device of claim 1, wherein the sheath assembly further comprises one or more devices capable of manipulating a tissue.

5. The device of claim 1, wherein the sheath assembly further comprises at least one reflective element configured to reflect ultrasonic energy.

6. The device of claim 1, wherein the sheath assembly further comprises at least one irrigation channel.

7. The device of claim 1, wherein the sheath assembly further comprises at least one aspiration channel.

8. The device of claim 1, wherein the sheath assembly further comprises at least one channel for delivering a therapeutic agent therethrough.

9. The device of claim 1, wherein the sheath assembly is adapted for use with an imaging system.

10. A method of modulating, focusing and directing a cavitational energy emitted from an ultrasonic probe vibrating in a direction transverse to a longitudinal axis of the ultrasonic probe for tissue ablation comprising:
    enclosing at least a portion of the ultrasonic probe within a sheath assembly comprising a sheath defining at least one fenestration between a proximal end and a distal end of the sheath;
    inserting the ultrasonic probe into a blood vessel;
    guiding the ultrasonic probe and the sheath assembly into the blood vessel and to a site of an occlusion;
    positioning the ultrasonic probe and the sheath assembly such that the at least one fenestration is in proximity with the occlusion;
    providing an ultrasonic excitation signal to the ultrasonic medical device and transferring the ultrasonic excitation signal along a length of the ultrasonic probe to a flexible probe tip, thereby causing a transverse vibration of the length of the ultrasonic probe and the flexible probe tip and a generation of a plurality of transverse nodes and anti-nodes of the cavitational energy along the length of the ultrasonic probe and the flexible probe tip; and
    controlling a selective transmission of cavitational energy through the at least one fenestration in the sheath, thereby directing the cavitational energy in an area of the occlusion within the blood vessel to cause fragmentation of the occlusion.

11. The method of claim 10, wherein the sheath assembly is capable of partially shielding tissue at a site of a surgical procedure from the ultrasonic probe.

12. The method of claim 10, further comprising removing at least one fragment of the occlusion through an aspiration conduit of the sheath assembly.

13. The method of claim 10, further comprising supplying an irrigating fluid to the site of the occlusion through an irrigation conduit of the sheath assembly.

14. The method of claim 10, further comprising delivering a therapeutic agent through a conduit of the sheath assembly.

15. The method of claim 10, further comprising positioning the ultrasonic probe proximal to the occlusion using an imaging system.

16. The method of claim 10, comprising manipulating tissue with a tissue manipulation device of the sheath assembly.

17. The method of claim 10, further comprising shielding an ultrasound energy emitted from the ultrasonic probe with the sheath assembly, and visualizing a surgical site with an ultrasound imaging system, the shielding of the ultrasound energy increasing the resolution of the surgical site visualized by the ultrasound imaging system.

18. The method of claim 10, further comprising introducing the sheath assembly from an exterior of a patient to the site of the occlusion, and introducing the ultrasonic probe into the sheath assembly and guiding the ultrasonic probe to a surgical site.

19. A medical device, comprising:
an ultrasonic probe configured to emit ultrasonic energy transversely along a portion of the ultrasonic probe; and
a sheath comprising a proximal end and a distal end, the sheath at least partially surrounding the ultrasonic probe and defining a fenestration between the proximal and distal ends of the sheath, the sheath being configured to substantially dampen ultrasonic energy such that ultrasonic energy delivered by the medical device is focused toward a region adjacent the fenestration.

20. The medical device of claim 19, wherein the sheath defines a plurality of fenestrations between the proximal and distal ends of the sheath.

21. The medical device of claim 19, wherein the fenestration extends from a proximal end of the sheath to a distal end of the sheath.

22. The medical device of claim 19, further comprising at least one reflective element disposed on an interior surface of the sheath.

23. The medical device of claim 19, wherein the sheath is at least partially surrounded by a second, retractable sheath.

24. The medical device of claim 19, wherein the sheath is constructed to substantially prevent ultrasonic energy from passing therethrough.

25. The medical device of claim 24, wherein the sheath comprises one or more materials that are capable of dissipating ultrasonic energy.

* * * * *

UNITED STATES PATENT AND TRADEMARK OFFICE
CERTIFICATE OF CORRECTION

| | | |
|---|---|---|
| PATENT NO. | : 7,503,895 B2 | Page 1 of 1 |
| APPLICATION NO. | : 10/373134 | |
| DATED | : March 17, 2009 | |
| INVENTOR(S) | : Robert A. Rabiner et al. | |

It is certified that error appears in the above-identified patent and that said Letters Patent is hereby corrected as shown below:

On the title page, item [75] "Inventors":
  delete "Robert A. Rabiner, Chelmsford, MA (US)" and replace with -- Robert A. Rabiner, North Reading, MA (US) --.

Claim 16, column 15, line 15:
  after "claim 10" add -- further --.

Signed and Sealed this

Fifth Day of May, 2009

JOHN DOLL
*Acting Director of the United States Patent and Trademark Office*